US012674803B2

(12) United States Patent
Shah et al.

(10) Patent No.: US 12,674,803 B2
(45) Date of Patent: Jul. 7, 2026

(54) **DIAGNOSIS OF *BABESIA* USING *BABESIA* RECOMBINANT PROTEINS**

(71) Applicant: ID-Fish Technology, Inc., Milpitas, CA (US)

(72) Inventors: Jyotsna S. Shah, Santa Clara, CA (US); Olivia Mark, San Jose, CA (US); Song Liu, San Jose, CA (US); Prerna Bhargava, Sunnyvale, CA (US); Hari-Hara Potula, San Jose, CA (US)

(73) Assignee: ID-Fish Technology, Inc., Milpitas, CA (US)

( * ) Notice: Subject to any disclaimer, the term of this patent is extended or adjusted under 35 U.S.C. 154(b) by 1090 days.

(21) Appl. No.: 17/726,839

(22) Filed: Apr. 22, 2022

(65) Prior Publication Data

US 2022/0341928 A1 Oct. 27, 2022

Related U.S. Application Data

(60) Provisional application No. 63/179,109, filed on Apr. 23, 2021.

(51) Int. Cl.
*G01N 33/569* (2006.01)
*G01N 33/547* (2006.01)

(52) U.S. Cl.
CPC ..... *G01N 33/56905* (2013.01); *G01N 33/547* (2013.01); *G01N 2469/20* (2013.01); *G01N 2800/26* (2013.01)

(58) Field of Classification Search
CPC ........... G01N 33/56905; G01N 33/547; G01N 2469/20; G01N 2800/26
See application file for complete search history.

(56) References Cited

U.S. PATENT DOCUMENTS

2009/0111123 A1 4/2009 Birkenmeyer et al.
2019/0277847 A1 9/2019 Shah et al.

FOREIGN PATENT DOCUMENTS

JP 2011500088 A 1/2011
WO WO-2013059795 A1 * 4/2013 ....... G01N 33/56905
WO 2019089936 A1 5/2019
WO WO-2020252313 A1 * 12/2020 ....... G01N 33/56905

OTHER PUBLICATIONS

Meredith et al. 2021 (Technologies for Detection of Babesia microti: Advances and Challenges; Pathogens 10: 1563). (Year: 2021).*
Sela-Culang et al. 2013 (The structural basis of antibody-antigen recognition; Frontiers in Immunology 4(302):1-13) (Year: 2013).*
International Search Report and Written Opinion for International Application No. PCT/US2022/025901 mailed Sep. 14, 2022, 12 pages.
Lodes, Michael J. et al: "Serological expression cloning of novel immunoreactive antigens of Babesia microti", Infection and Immunity, American Society for Microbiology, US, vol. 68, No. 5, (May 1, 2000), pp. 2783-2790, XP002142776, ISSN: 0019-9567, DOI: 10.1128/IAI.68.5.2783-2790.2000.
Partial Supplementary European Search Report of the European Patent Office dated Jan. 3, 2025 from corresponding European Patent Application No. 22792558.3.
Precigout, E. et al., "Association between sequence polymorphism in an epitope of Babesia divergens Bd37 exoantigen and protection induced by passive transfer", International Journal of Parasitology 34 (2004) 585-593.
Verma, N. et al., "Antigen Discovery, Bioinformatics and Biological Characterization of Novel Immunodominant Babesia microti Antigens", Sci Rep 10, 9598 (2020). https://doi.org/10.1038/s41598-020-66273-6.
Elton, Catherine M., et al., A library of recombinant Babesia microtic cell surface and secreted proteins for diagnostics discovery and reverse vaccinology., International journal for parasitology, Elsevier, 2019, 49(2), 115-125.
Office Action from the Japan Patent Office mailed Feb. 4, 2026 for corrsponding Japanese patent application No. 2023-564161, 11 pages.

* cited by examiner

*Primary Examiner* — Mary Maille Lyons
(74) *Attorney, Agent, or Firm* — Pierce Atwood LLP; Christopher A. Baxter

(57) ABSTRACT

The disclosure, in some aspects, provides a composition comprising labelled and/or tagged and/or bound amino acid sequences useful for the detection of *Babesia* species. Also disclosed are methods for the detection of infection by one or more *Babesia* species.

16 Claims, 4 Drawing Sheets

Specification includes a Sequence Listing.

Figure 4

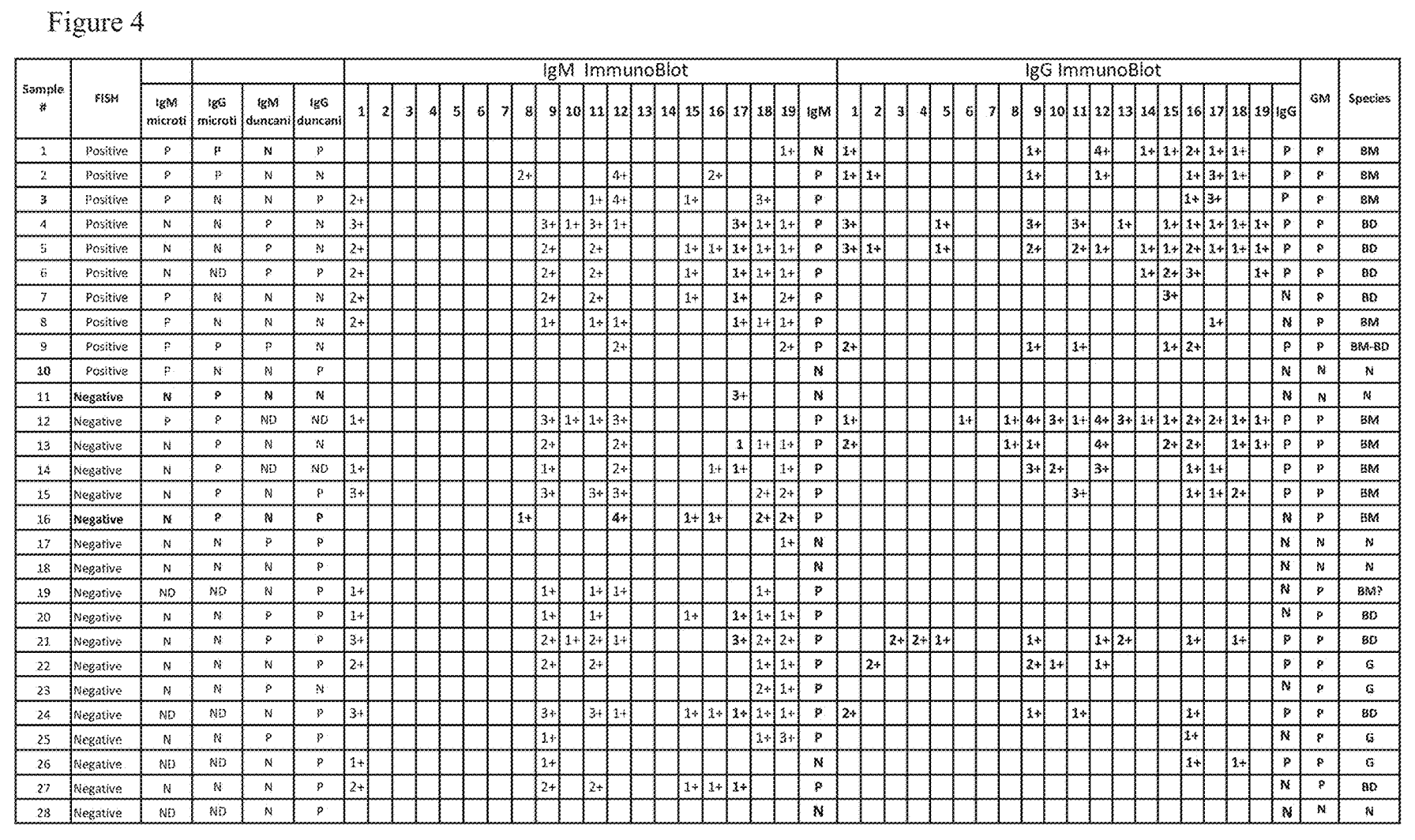

Figure 4. Table comparing FISH results, IgM and IgG microti/duncani serology, IgM and IgG ImmunoBlot banding patterns (bands 1–19), GM, and Species for Samples 1–28.

DIAGNOSIS OF *BABESIA* USING *BABESIA* RECOMBINANT PROTEINS

FIELD OF THE INVENTION

Aspects of the present disclosure provide novel compositions and methods for identifying antibodies resulting from infection by *Babesia* species.

SEQUENCE LISTING

The instant application incorporates by reference the Sequence Listing in the ASCII text file filed Apr. 22, 2022, entitled "0153-2018US02-Sequence Listing-ST25.txt", which was created in Mar. 1, 2022 the size of which file is 81.819 bytes.

BACKGROUND

Apicomplexan protozoan parasites of the genus *Babesia* cause babesiosis in humans and animals. There were 2,161 cases of human babesiosis reported in the USA in 2018 to the US Centers for Disease Control and Prevention (CDC). *Ixodes scapularis, I. ricimus, I. persulcatus* and *Dermacentor albipicius* are some hard ticks that transmit babesiosis to humans after acquiring *Babesia* species from reservoir animals such as white-footed mice and mule deer. Human to human transmission of *Babesia* species can occur through blood transfusion, congenital transmission, and organ transplantation. *Babesia microti, B. duncani,* and *B. divergens* are mainly responsible for human babesiosis in the USA, with *B. micron* and *B. duncani* considered to be, respectively, more prevalent in the East and West coasts of North America *Babesia microti, B. divergens, B. venatorum* and *B. crasser* are responsible for babesiosis in Eurasia. Babesiosis is also prevalent in Africa, Australia, and South America.

The two main approaches for diagnosing human babesiosis in a clinical laboratory are the detection of parasites in blood and assaying antibodies produced against the parasite. Parasites in peripheral blood are frequently detected by examining stained blood smears by microscopy. However this method cannot identify *Babesia* parasites at the species level. Alternatively, *Babesia* parasite nucleic acids are detected by qPCR on blood samples and the detection of ribosomal RNA within infected red blood cells (iRBCs) by fluorescence in situ hybridization (FISH). Several qPCR tests have been developed for *B. microti* and may be used for screening blood for transfusion. A qPCR test for *B. duncani* has been recently developed, but is not yet in common use. *Babesia* genus-specific FISH is used to detect *B. duncani* and *B. microti* in blood and provides laboratory confirmation of babesiosis with lower resource and shorter time requirements than qPCR tests, a lower sensitivity of detection. However, *Babesia* parasite concentrations in peripheral blood can be low very early in an infection and during chronic low grade infections where parasites may be sequestered by binding to capillary endothelia in internal organs, Cytoadherence to the capillary endothelium has been reported in *B. duncani*, and cytoadherence and the variant antigens on the surface of infected red blood cells (iRBCs) that are responsible for it have been characterized in the bovine parasite *Babesia basis.*

Serum antibodies are commonly detected by immunofluorescence assays (IFA) performed with *B. microti* fixed on microscope slides, but an equivalent IFA has not been widely used for detecting antibodies against *B. duncani.* An ELISA utilizing recombinant proteins as antigens that has been recently developed for *B. microti* is less sensitive than IFA and is not yet in common use for diagnosis. There is presently no report of an ELISA test for *B. duncani.* Immunochromatography-based lateral flow tests have been recently trialed for point-of-care diagnosis of bovine babesiosis, but similar tests are not yet available for human babesiosis. IgM is the first antibody class to be formed in a primary immune response. IgM antibodies are produced early, usually within days, during an infection before class switching later to higher affinity IgG and other immunoglobulin classes. Serum antibodies may therefore be below the threshold of detection in the very early stages of an infection. As the infection resolves, either as a result of the immune response or through drug treatment, antibody levels begin to diminish but can persist at detectable levels for several months. A total immunoglobulin or IgG IFA titer of ≥1:256 is recognized by the CDC as laboratory evidence that supports a diagnosis of babesiosis. IgM IFA titers of ≥1:32 have been, however, reported to have high sensitivity and specificity for acute or early *Babesia* infections. Detection of anti-*Babesia* antibodies per se does not differentiate between an active or ongoing infection and a resolved past infection, although high IgG antibody titers indicate a probable active indication. A marked increase in HA titers over time in a patient is a better indicator of an active infection, but the required temporal follow-up in serum collection and testing is often not easily possible. Therefore, a simple, quick, and reliable test for *Babesia* is a high priority.

BRIEF DESCRIPTION OF THE DRAWINGS

FIG. 4 presents a chart showing *Babesia* IB results for patient samples previously tested with FISH and IFA assays. Band intensity was recorded as 1+, 2+, 3+, or 4+, and intensities of 1+ and above were scored as positive. P, positive; N, negative.

SUMMARY

Figure 1:
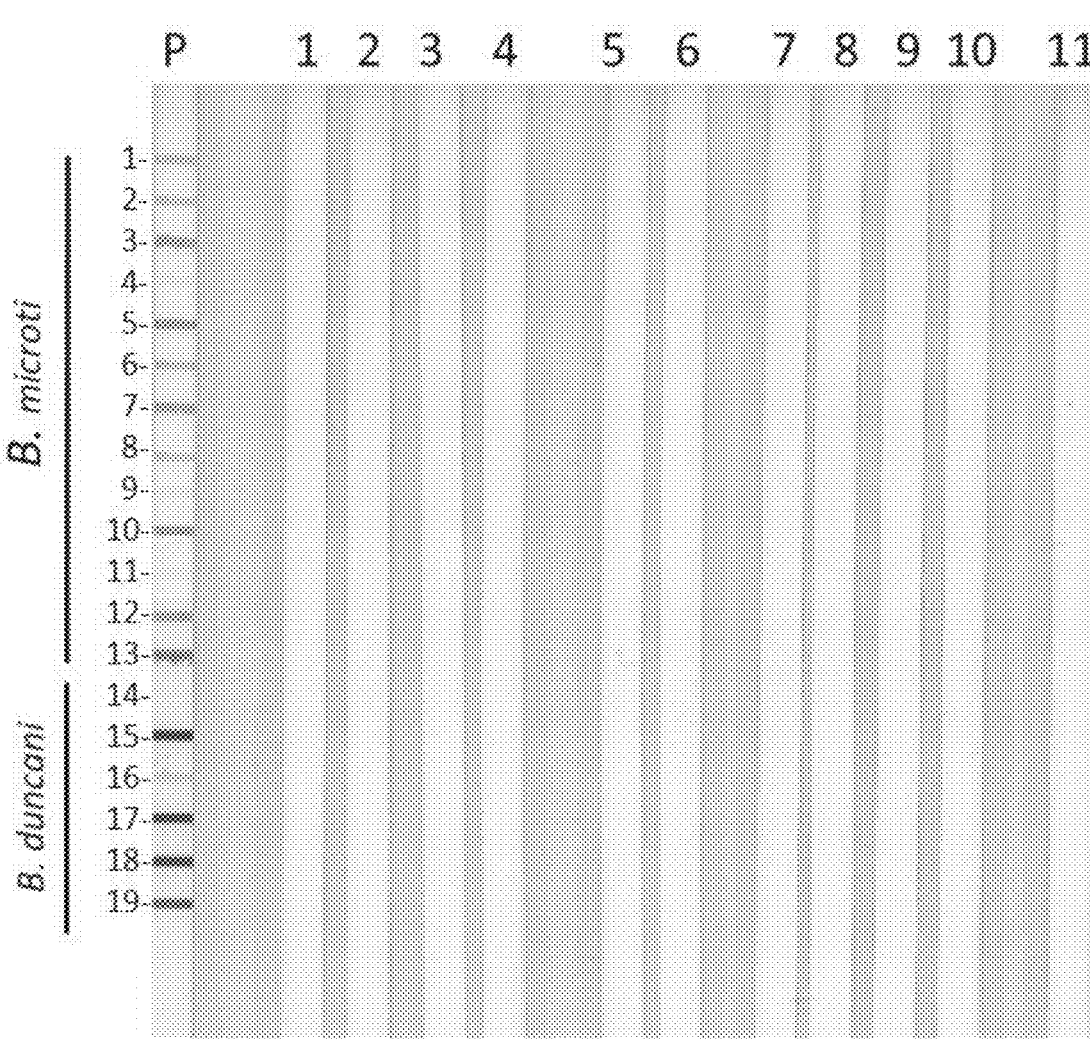
FIG. 1 presents a photomicrographic image showing *Babesia* ImmunoBlot strips tested with rabbit anti-sera with antibodies to the following pathogens: P—Positive Control (*Babesia*); (1) *Borrelia burgdorferi* B31 and (2) *B. burgdorferi* 297; Tick-Borne Relapsing Fever *Borrelia* species (3) *B. hermsii,* (4) *B. turcica,* (5) *B. coriaceae,* (6) *B. miyamotoi; Bartonella* species (7) *B. elizabethae,* (8) *B. henselae,* (9) *B. vinsonii,* and (10) *B. quintana*; and (11) *E. coli.* M, IgM; g, IgG.

According to an aspect of the disclosure, a composition is provided, the composition including labelled and/or tagged and/or bound amino acid sequences, wherein the labelled and/or tagged and/or bound amino acid sequences include amino acid sequences SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19, and variants thereof which retain the immunological binding profile of the corresponding non-variant. In some aspects, the bound amino acid sequences are bound to a substance (i.e. a solid support) selected from the group consisting of nitrocellulose, nylon, polyvinylidene difluoride (PVDF), plastic, metal, magnetic beads, and agarose.

According to another aspect of the disclosure, a method for detecting infection by one or more *Babesia* species, if present in a biological sample obtained from a subject suspected of having a *Babesia* infection, is provided, the method including: (a) providing a composition including labelled and/or tagged and/or bound amino acid sequences, wherein the labelled and/or tagged and/or bound amino acid sequences include amino acid sequences SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19, and variants thereof which retain the immunological binding profile of the corresponding non-variant; (b) providing the biological sample obtained from the subject suspected of having a *Babesia* infection; (c) contacting the biological sample with the composition of step (a) under conditions appropriate for specific antibody binding to an epitope; and (d) detecting specific binding of IgM- and/or IgG-class antibodies, if present in the biological sample, with the amino acid sequences of step (a), wherein the sample is scored as positive for infection by one or more *Babesia* species when: (i) a positive immunobinding reaction with IgM-class antibodies is detected for at least two of the amino acid sequences of step (a), or (ii) a positive immunobinding reaction with IgG-class antibodies is detected for at least two of the amino acid sequences of step (a), and wherein a positive score for infection indicates infection by one or more *Babesia* species in the subject. In some aspects, the binding of IgM-class antibodies is detected through the use of an anti-human IgM antibody linked to a detectable moiety. In other aspects, the binding of IgG-class antibodies is detected through the use of an anti-human IgG antibody linked to a detectable moiety. In some aspects, the detectable moiety is selected from the group consisting of chromophores, radioactive moieties, and enzymes. In some aspects, the detectable moiety includes alkaline phosphatase. In other aspects, the detectable moiety includes biotin. In some aspects, the *Babesia* genus includes species selected from *B. micron*, *B. duncani*, B. MO1, *B. divergens*, *B. venatorum*, and *B. crassa*.

According to yet another aspect of the disclosure, a method for detecting species-specific infection by *B. microti* and/or *B. duncani*, if present in a biological sample obtained from a subject suspected of having a *Babesia* infection, is provided, the method including: (a) providing a composition including labelled and/or tagged and/or bound amino acid sequences, wherein the labelled and/or tagged and/or bound amino acid sequences include amino acid sequences SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19, and variants thereof which retain the immunological binding profile of the corresponding non-variant; (b) providing the biological sample obtained from the subject suspected of having a *Babesia* infection; (c) contacting the biological sample with the composition of step a) under conditions appropriate for specific antibody binding to an epitope; and (d) detecting specific binding of IgM- and/or IgG-class antibodies, if present in the biological sample, with the amino acid sequences of step (a), wherein: (i) the sample is scored as positive for infection by *B. microti* when a positive immunobinding reaction with IgM- or IgG-class antibodies is detected for at least one of SEQ ID NOs: 1-7, 9, 11, or 13 and at least one of SEQ ID NOs: 8, 10, or 12, or (ii) the sample is scored as positive for infection by *B. duncani* when a positive immunobinding reaction with IgM- or IgG-class antibodies is detected for at least one of SEQ ID NOs: 1-7, 9, 11, 13, or 16-19 and at least one of SEQ ID NOs: 14 or 15, and wherein a positive score indicates infection by *B. microti* and/or *B. duncani*. In some aspects, the binding of IgM-class antibodies is detected through the use of an anti-human IgM antibody linked to a detectable moiety. In other aspects, the binding of IgG-class antibodies is detected through the use of an anti-human IgG antibody linked to a detectable moiety. In some aspects, the detectable moiety is selected from the group consisting of chromophores, radioactive moieties, and enzymes. In some aspects, the detectable moiety includes alkaline phosphatase. In other aspects, the detectable moiety includes biotin.

DESCRIPTION OF THE SEQUENCES

B. microti Bm8630

SEQ ID NO: 1

MHNSNIFRIGILYTLGLIIINGPIIVSANTPQKVNEQKNDYFYVDGVKYRNPSNEHPACRGNV

DLVIIVKWPGGLDKYSWSEKIAEYLPKFVSQLEISENRFRVGLIMSHTYDKDFLVDLNGEHSL

DKTKLLEEVEKSVNVSNFVIGTKLEKMLNVAYLMFKKSKRLNTVKMIYLISDGMYISDEEVEK

VLNKVRAYPIQVYVQGIGETSKLWLKPHMGCTLDNSYPCPNFMYSKIDEPLEPKDAYTRMCLG

MPQNAVCFIQYGEFNSCKLPCSPYSVKSALATSYTTLRGPTFGYVGFKPGVDCKMQAHFKDMK

FKKCTLKDCMTDEEYAEYLNNKKKNNRIDIKNAVTPIMDKDKGSKSTIDEKSPTGEETDTSDK

-continued

```
SQTETGETVEEIDETITDGTEETDTSDKSQTETGETVEEIDETITDGTEETDTSDKSQTETGE

TVEEIDETITDGTEETDTSDKSQAETGKTVETTTNNTSDTINTSGGTDKSQAETGKTVETTTN

NTSDTINTSGGTDKSQTETGKTVETTTNNTSDTINTSGGTDKSQAETGKTVETTTNNTSDTIN

TSGGTDKIGPNHPINNNTFKTPIHKVDHKSPENVEESKEKHEANKHADSTKDTNGENKGNESK

NKFLSTANKVKNALFYTANTRKLVSDKPETIESNVSVKSTNHSNKNVAGDNNSNPKHNNADEV

IKINNGHSEAHTDDFESSNDVHTMSIGNQNVKIAGGVVGGVVIFGLVALAFANKRKQSTGYGY

TGLVYGDEDDEIKYDENPEEFTVTGIDDALWGEK.
```

*B. microti* Bm5294

SEQ ID NO: 2

```
MMKFLHITVITFLYLLNVYLISGHNILGNIPDKKTFREEQDVLKSALEDGMVILFESEFISRA

RPASDNSATNDNLSSEEHSNDNNLEKIDDKKRNELRKDAKVMSEVILKRREGELSTIPKKDGT

LHIMWKLIFYILYSRSGKWLFNNPSDMNLKDAKPGHHKVLKSTPAHIDNNIPLPEQQIYSISN

IPEVLPEKNGKTPILLFGMEAFVIFHLINQAMLEIVNSSDPIEEKVLFSEQWVHFVKHHFFIF

FPYNAITSKRCVRLLSDNTLESEMELLDVCKSLAEKSEKSDLLETFIMIDPENNGDLLEKCIN

EKHIIPSYMKLNHEKLSHLHLKHNLAMELSDFISTYGMIMTNAEQEIFKDNNILNSKFWGAKC

TKDEAIKAENEIIKLFSNIQKDLNGVITKTFQKLLDLLEKNGGNIKSGPAKSLIKAENNEFQA

AKKECESNNELKKNIEEAKTQFLKYAADGSSGGEELVKELANNELSEWKFNVSAHILDTMNKT

CEEDSAFCLSAIKHCRKSLEGLESDTEQYKIIEKLHRALSAALLKSGKLNEKDYIEELSGYIK

HDQNELSTDKPQQSSMLQIRMARIRRHKI.
```

*B. microti* Bm4855

SEQ ID NO: 3

```
MTVTTIALTVSIVSYIHGSPSNGLYESNLFYTEGYGKYLTSPTKIKTIEFGGYKFEFDDDTLP

VTSITKIDVITYDDKPILFEFISDKDRPYRRFYYYTLDSKTNKLYNYVTAETGYNVEDSSGLK

YYTELSKSGINDVLQDLDKNIDESNIEHLKTSYVTKGLNIAIEVYSNRVVEQIKSIKVVTPVE

LFDYKTEVPIESVDHESRDNSLAEVEEDGKAVQVGTQPVYEVNDGAHNPSAQVLSQNNIIETL

DDKSKVTHLRNAGSEKIRV.
```

*B. microti* Bm0985

SEQ ID NO: 4

```
MINLIIFLPTVLSYVSIVYASESDLGGLLSVHQVTNAENLYELGIKQLDSSIKLLEDAKFTGN

RILRDYEQTVQYVAAHIGPSGSFIKFSPVIKRLISQINTLTHGLNDALSHVDPFLSKLMNEKS

QLVANKNVISQGAEENISKLSTQSARNLLISIKKSLQTLELGELNSRKLNTIAEKIGTDVRHA

IKSTNSTLNILLGYRVTFTLVIDSENILSDSEKFKINIFSHSKLCHGTTNEVVNLQHKAKMLF

QKSLSEGLLHEDINMGKNYIIRIDSYAHESNKLASEMNAKNYAMASSVRFIRKDIDKLKRILD

DYKNSPHSAYKRMDVIHVEIDKIYESIGTALKWANAAVKSNFSILTATRETYQALENLLKISK

KSHSIRSTYTTQLDADSNSGPFYASTTAIGDKHDPDDLYGLKHSGYNTSNNDSSSRYSYYVKK

FGGHGSRSNHSTSESGEDDCLNDKCCKNCEKSKPWYKRFGLGSVISGIQNMFGASYQQDHSDD

DHYPKFPHSPYIIPTAPPIDLVPNDIHTNTRSNIIKNGVTEKVIPMSSPNSAQSDHEKKEPTS

DDNKNDPVDTNSTKIEDVAETKSSIETETVSNDLENKAAETEESIDTEPYESESVGTKSSTGI

DNDTTVDQNSGNGHNAIKTTNNPHIQSVNPDFQPENPNNPHVNHYGSFEIQANIFGNQGNLEN

IQRLQQDPKINELIIKGKEFFELFNAVKMKLMRGSSYLNSKMVSIMLAKIFQGSLSNLCYNFN

QNRYYYDTQAYNSALSN.
```

*B. microti* Bm1510

SEQ ID NO: 5

```
MFNFLEISRVFTTLTILSCIFSYVSASSPSYCDAPSGFTVINVTSLLDGTPLPIGITLETDKS

GYNYFTVDRTLPQYKKVGFCLNGYLDTFDTPKVQTILHKKFEDSVYVSYIDKFVTNVDGNAPI
```

-continued

CTLTHAYSLYGGDITSALPPFTVRKISDGFLSRLNERKQLSSICSTACGGLVDVVGGNYPKGS

DIVPHSESVDKVKFSDVLVKSLTLKCGDHTFYNFDRDQFAYMYLFEHDGAKYAALSRLTPTMI

EVAVMCKYGNGVEEKLLYDNDSEFQQAVLKLVPINIFIENTSSMPHGASMTKLDENIDEIAIN

RFVLRYPYVLLPGLAVDIGKGNADTIWIVKPSEEDSEVKYFVVFG.

*B. microti* Bm0320

SEQ ID NO: 6

MKLFYVWVSLAFLGSTIVTGRPANSNDYLTTSSSDSDSSESESELDGLSDLEDASDAEFDDIY

NVEDLTSNVDGNLAKFGHFDGKDTKNEDTSASLDLNKWNNSSRKKSGNKVKFSSNKSKSTTKK

KRKKTYSTNENGNKLKFEDKKHVEHKKLSSKKKLKQQQLNEQHGIKPINASNDTDMKHGLKSG

KSSSKHGIKAHTFDSQTHIITNQIGTDQIQLRDSEIENKVYKKLVAELNKTPDLDIAGISESI

RYLGSGYDIIFGNPIGDPLMMVDPGYRNPIIQLEWDKHSTFAHNNSLPQPVDGWVRPEISCKQ

AEKVDHVNTLEDYKKELSVDAVASSDFLNFFAFSASGGYKNFAKLVTQEKTRSFILKTYCLRY

IAGLEVSTNLKLTPAFKNAVDKLPVIFDGFEEYSSCPIEKYKANESDTDCESNVRPWMDFFKE

FGTHFTSVVHLGGKMTYQVQMKQSDINKLQEQGVNVDAAIKATCGFGMPNISGKISTKGESTS

ISKMSDYKVEKMIMVIGGEPPKDLNDSSNLNNWAKSVAKSPMPIKSELIPIRELFDLHELQQS

YNQAIKYYSEVYGISQNDMYEIKGKIKGIPEIIKEAQQVTYDGPAPGRVVCPIGTTILFGFSM

TITKKKKALDFLKNTSYNVNIVPCVVGNEKCSGTAQSDSIVKIWALCSPHPAPLLVQVSSHKN

NGPATVECPKGFVIGMGFGITFPKGLPIMPQDIYPCRNGQTSCTKIPDKDGSTTVWAVCFESG

AIEVDNLTNNAKAGSSASCEAHDHITSGLVNTCPDDYEVLCGFSMALTRKNSHTDDHFKACRG

GKSCAIDKHKRHDNECIAYASWNVCSLVVPGHKDTVHPARANVTLDRTKTANGIEPIGKN.

*B. microti* Bm9435

SEQ ID NO: 7

MSLWYAVILALGYINSECKNVNRSIRSKVYNNHSNDMPINPVKVQHQKHNPWRTKFMKFDSDN

EEEGNENDHDEDNVEEGEEVLDSEKSKTSSHIVNPTGTSKDDNTIENDNEYKPRVCGQGKRGI

LIYQQQDYGIAIMGLIDKGTLKLYAGNIILKEISLWNIISPIEMANNKCFSIRQPTQLPTILC

AGGIDSRNRWVNALESSRLCLITKVKYYLPISIDKDFVEPEDPPPSGINVF1AESQFGKPEIV

INGKTLEQIKNDEMESISTSDEYGTTLWNGELQKPDFQEDEFNGDESMESLAEAEMKKDIAPE

FGHARMF.

*B. microti* Bm2975

SEQ ID NO: 8

MKGIGPLSTIYVLSAIIGVSIGVRVGVMQHNKKPKVVNAVHNVYASLIDTNSSNSVTPTASTQ

KNTTENTNTTTPDPNVNSTDTKEKDNNATEIDDKSINPKCIGEIIKPFSIESKTFTIHGGGAG

VENSGKWISNASDIDTNLETFLTIKFEMNSQIYSYINDLGQNMTATINLKMSPDLKDFGYSCP

KNTVSVVDGEFSNVETLLTEKLKFFSGVFNKETNRVDIDITKLIRDKFLGVGDSGENVLNLAV

KSGNKCIYRIHFKENPPTIKIIPKNTTYIQTDKWTACSKECKKEGAYQCAPIKCIEGNEKCDT

TKMFSKRECVDVEDCVNVEEHINTKNSIGGWDLNLSNIFLKSPLYIGLCVALVILLAIAGIVV

FQKMKGQKYVQITDEEIVGSVFTGGCI.

*B. microti* Bm3280

SEQ ID NO: 9

MVNLSIPGLLLLSAYSLNSASAGDVYEISSGNPPDIEPTSTSLETNVVTNYIPEPNADSESVH

VEIQEHDNINPQDACDSEPLEQMDSDTRVLPESLDEGVPHQFSRLGHHSDMASDINDEEPSFK

IGENDIIQPPWEDTAPYHSIDDEELDNLMRLTAQETSDDHEEGNGKLNTNKSEKTERKSHDTQ

TPQEIYEELDNLLRLTAQEIYEERKEGHGKPNTNKSEKAERKSHDTQTTQEICEECEEGHDKI

NKNKSGNAGIKSYDTQTPQETSDAHEEGHDEINTNKSEKAERKSHDTQTTQEICEECEEGHDK

-continued

INKNKSGNAGIKSYDTQTPQETSDAHEEEHGNLNKNKSGKAGIKSHNTQTPLKKKDFCKEGCH

GCNNKPEDNERDPSSPDDDGGCECGMTNHFVFDYKTTLLLKSLKTETSTHYYIAMAAIFTISL

FPCMFKAFRAIISHKLRKNGSNAKLALSMFLSFIFSLIILTLDYGLMLLAMTFNVGYFFAIII

GSSLSYTMFGLLFDSPCDCGGKKAILSDCCG.

B. microti Bm3430

SEQ ID NO: 10
MGYLSLNIIVTSLVTLVANVSAVLPDILSQNNTFKSFLEVNNVDQEDLICNKALCKSTDSINR

NTSSYCYKYKLCSKCSVSNVPDHPVCYLLDNDHNYIHLMEGHLGSQPIGSANSHDNSSHDEHS

SHSNNGDMMDEHEEENFLQEYESKSMKFIPTSNMSDFDHARRSCAVDSKGNVMISVRLIIQWY

MSKDKSNNQQHHGNDDDSQNYDANYLQLTPMYSDDSVNSSMLEMDHDDSESSNSHKSRMANMA

KNFQVLKNIHKSAVKRYKSPKAKIYLIFSNPKINSCRHPVIYNGKISPSSMFVAKLESTISQI

DLTQDLIKSSIETIVSCEACDKLKYNSCIQVTCAKNTPGAASLAMGSAVYVPMTNTTIGVNAH

NPNAVVAAGIPMGKIPVIPHPAAISGGNVGHLNNGLHKAVNNAVMMPNGTSLPVQSGVVIKSL

YNCLAFLLTILYLNF

B. microti Bm0690

SEQ ID NO: 11
MEVERILFKSTIFLMFIRYTNAILFDTYLQVVSENDCNPKCLQGHTCILNRKTNKKSCTCPPN

HYYDENFGCQMVITCPLCRHANPWGTTHTVPNTALPGQHKSGYQYSICKDGHTKDEMRTFCRR

YNACERGAKICPEHSTCIIDNKGHAVCNLDNGYRWHDNTKKGAVRIEYCGGHNKNKCIPPATC

QEVNNANSNTLTVCSCPSEMYLTRNKRQCSKQQQFSDNKVYSISVKNRTEKFPENFKVFLDGC

FDVQLDGKEGVVIYKSSDTVSSIKSIVNIPTDLKSIHFEMKFKTLNIFVENGNDMHPIFSIKF

DHSDCKFIESIEGLEIGDDILRTESNMRDLHPTL.

B. microti BMGP112

SEQ ID NO: 12
MVSFKPTIITAFAAFLAFGNISPVLSAGGSGGNGGNGGGHQEQNNANDSSNPTGAGGQPNNES

KKKAVKLDLDLMKETKNVCTTVNTKLVGKAKSKLNKLEGESHKEYVAEKTKEIDEKNKKFNEN

LVKIEKRKKIKVPADTGAEVDAVDDGVAGALSDLSSDISAIKTLTDDVSEKVSENLKDDEASA

TEHTDIKEKATLLQESCNGIGTILDKLAEYLNNDTTQNIKKEFDERKKNLTSLKTKVENKDED

YVTHFRDMATEAQNAVGEVKKAIDAVVAHRKAENLDVDDTLFSNLSTLLDTIIETSRAYLPGV

AFALLSSVAMFLF.

B. microti BMIPA48

SEQ ID NO: 13
MRGMFSNKWMSFVCFSILFVALKSDLEYVSALKLLRAPPQTSLFLEKLIDDGSDIPKDPIDTD

KEESQSSLFKFNLNLFNKKSIWEADEKFVITLAKSRLNVILAQKLDKFLAKTCKIYTVDSEHS

ACINDIKIYAQKCIESNDLNSCYVIPIQPIAKLPTSRLYGLVPHVLNFSILIFTNLRSNLDRY

YIDGSKDWFSHIFMRLKRFFGIRNKHSYFSDNRLMNKIFSRTSTTFGPDRSDSLLSNYIKFGA

IEYAILLNTRSNLVKMILSSFAHIKFVRKRLYKFYTNKWKSIEGLVTRGHLKPVDLSNNPISD

NIFKYFGKFSNNTNLSNAIAGAFLDHYKSLFSNSTDVNGEGSSGEGPSGEGFNGEGSSGEGPS

GEGFNGEGFDGEGPSGEGPSGEGFNGEGFNGEGLNGEGPSGEGPSGEGLNEWNGLMNGTA.

B. duncani BdGPI6

SEQ ID NO: 14
MARFFSYKKLIAFAIVALASLKEVSFLGGCPYALAVATTTTTGTNGAATGTNGAATGTNGAGA

NDTSKNTSDPNTPATPPSSPESNKDNAAGGSDGQKPTGQDPQKPNAGNGFAATSVIGAATIGL

LTLAFN.

-continued

B. duncani BdGPI8

SEQ ID NO: 15

MNLKWLLGLALIGSKYALGGDPNDSEVDSGKERGPGKRMTFDELLDELKTAEASVLGIKAEIN

GGLNRLRYRIGNLDAITKSDYDEISDAIRDIITKRTEFAKAVNKRVQLEAIANKFSERTSMGN

LEDIQFSTFWVKLEAITRVPDFQLKEDFVKMKDEIIDVKEKFIEKLKKAREATAEVIPETIVE

DQEMKSDLHEEIKSHGDDDIFNDKSDKKQNSGFAATSSSLILLAMATIGYSLF.

B. duncani BdGPI17

SEQ ID NO: 16

MDVFSILLVFSAFYVNAIAADDVKTFLFKKDVESTVEIDANDDAVLVCPIASVLIIKKARWLP

VTGGDMRVKDGFSRTTRIGWLCNGLENCAFRPVAHLSKIGDRYEFLGQPIETDIYKLTVTATC

GNFMFKRPGRREMLCIPTSAKPDIVLGCKDNEAIELSYVRVGGKSKHQWRHRDYCAESIIKTA

HPLCTGKKTCKIAHDVFLKNAKECIPREFNVEYYCAAPHKNSFYDPLDAVVVDGVSVATKYVL

TAEDGARASAKTNAYQVLQVDSALWESDGATERRDRLELVKFLCDGRAECVFSPTRSIIGPDE

RKCNDVVFGGMVKDTMSHFMLRAHFSLVPFDPKKYDEKEYHHVTIKSTEKKTLECPVNMSLTF

YVALWGGKITDTSPLKGPKHFVEVDINGEKHRYSEIINIVGTQCFGKSKCEIEPLKLKPPRHE

KDLKEFPTHEGVKKDDHQLELYYKCIDLQTLPSLVESLISDGPRYPREFITPIQLSPDMRIVV

MLDIYGPTVLEVANALKLEIPVARTNEIKISWKDAKISQGIRLVKDTRNYVFEFVIGAEDYIH

MTVNSFDNDGSPMSIPVEFEASKRILDFSRGIEDFVVATGEITNFRAFIKS.

B. duncani BdHSP-70-1

SEQ ID NO: 17

MAATAIGIDLGTTYSCVAVYKDNNVEIIPNDQGNRTTPSYVAFTDTERLVGDAAKNQEARNPE

NTVFDVKRLIGRRFDDPTVQSDMKHWPFKVNAGAGCKPTIEVTFEGQKKTFHPEEISSMVLIK

MKEIAEAYLGRPVTDAVITVPAYFNDSQRQATKDAGTIAGLNVMRIINEPTAAAIAYGLDKKG

STEKNILIFDLGGGTFDVSILTIEDGIFEVKATTGDTHLGGEDFDNVLVEHCVRDFMRMNGGK

NLATNKRALRRLRTHCERAKRVLSSSTQATIELDSLFEGIDYNTTISRARFEEMCNEKFRSTL

IPVEKALRDADMDKRKINEVVLVGGSTRIPKIQQLIKDFFNGKEPSRSINPDEAVAYGAAVQA

AVLSGNQSEKIQELLLLDVAPLSLGLETAGGVMTVLIKRNTTIPTKKTQIFTTNEDRQEGVLI

QVFEGERAMTKDNNLLGKFHLSGIAPAPRGVPQIEVTFDIDANGILNVTAMDKSTGKSEQVTI

TNDKGRLSQTDIDRMVAEAEKFKEEDERRKCCIESKHKLENYLYSMRSTLNEDAVKQKLSTEE

LQNGLNTVEEAIKWVENNQLANQDEFEDKLKEVEKACAPLTAKMYQAAGGAGAGGMPGNFGGA

AAPPSGGPTVEEVD.

B. duncani BdHSP-70-2

SEQ ID NO: 18

MQMFNRFLKASVALLAVASFGIQYIFAKGSNSGKIEGPIIGIDLGTTYSCVGIYKNGRVEIIA

NEMGNRITPSYVSFVEGTQKVGEAAKSEATINTESTVFDVKRLIGRKFTDRDVQEDMKLLPYK

IINKSTRPYISLHDGKEQRTFAPEEISAMVLKKMKQVAESYLGKEVKKAIITVPAYFNDSQRQ

STKDAGAIAGLDVVRIINEPTAAAIAYGLDKANAESNILVYDLGGGTFDVSVLTLDSGVFEVI

ATGGDTHLGGEDFDRRVMDHFIDIFKKKHKVNIRDNKQSLQKLRKEVEAAKRTLSSTTEVLVE

VENLINGIDFSEKLTRAKFESLNAELFEKTLATVKKVVEDADIPIRDINQVVLVGGSTRIPRI

REMIKEYFGKEPDYGINPDEAVAFGAAMQGGILSGESSDNLLLLDVCPLSLGIETLGEVMSVI

IPRNTMIPAHKSQVFSTSVDNQPMVTIKVYQGERKLTKDNVILGKFDLSGIPPAPRGVPQIEV

TFDIDTNGILSVSAEEKGSGNKHNIVITPDKGRLSPEEIERMIKDAEMNAEKDKEVFNRVQAR

QALEGYIDSMTKTINDDKTGKKLEDDEKEKIRDALDEGTKWLASNPEVGADEISAKQHEIEAI

CNPIISKLYGSGEDSDDSGYSDEL.

-continued

```
B. duncani BdHSP-70-3
                                                       SEQ ID NO: 19
MADRFTGRNNREAVVAYPGWFSETQKQCLRACVTASGLSCLRVISHVHAMAMDYGVYRVKQLN

DETPTRVALVMIGHCHASAAIVDFYASHCSILSQVSRRNLGGRNLDMMLMKYMATEFSKKYHC

DPLENNKTRLKVEAVAVKTRRVLSANAESSYSAECLMEDNDMSGHITRTQFEEMCNAEFIPQL

IEMLKECIEASRTDLDSIFSVEIAGGSSRIPCIQQAISSIFNKVPSRTLNADECIARGCVLEA

AIKSNHYRVREYKTRLTLPRSLTLGYFNGQEPMLLEAIAAGTPLGDPIRVTLQAQAPVCVRVA

LGDALDPRSQDALGTLDIARHISQEAQPAPVTTNDGAAIQTDEQDAEIQSESSPSGGISVTLG

FDDCGQFVASPECCEYRWLPATILDIARLEAAELEARGRDLKENSRLQALNDFETLLYTVRDK

MQSSHRDFIDPQMIPAYESELDHWREWLYENSGASQETLQEGIDKVSSEWKRIDKYFKEHQNK

LENLEPFLQRLQERYNFCCEDNNPNWHGATPEERLNFAQELMDLDSRVRQMHQDESQRPRHME

PLFTMQQIQGEMQKLLVSISEFCQAKAAKAPAQEPPEQQPKEQQE.
```

DETAILED DESCRIPTION

The present disclosure provides novel compositions and methods for diagnosing, and treating babesiosis resulting from infection by diverse *Babesia* species. To assess the impact of testing limitations and to identify exposure to *Babesia* species, a recently developed modified Western Blot procedure was employed. The procedure, termed the line immunoblot (also referred to herein as "immunoblot" or "IB"), uses recombinant antigens from multiple *Babesia* species for the serological diagnosis of *Babesia* infection. As discussed in greater detail elsewhere herein, testing was conducted on patients with suspected babesiosis. Positive immunoblots were further characterized at the species level for *B. microti* and *B. duncani*.

Aspects of the instant disclosure provide compositions and methods for quickly, easily, and accurately detecting *Babesia* antibodies in a biological sample from a subject suspected of having babesiosis, thereby satisfying the need for such a test. Because multiple *Babesia* species have pathogenic potential for babesiosis, tests for *Babesia* species should be inclusive—that is, a test should be able to detect antibodies to multiple species from the *Babesia* genus concurrently. The present disclosure provides for antigenic amino acid sequences specific for various *Babesia* species. The amino acid sequences of the present disclosure encode antigenic peptides that have high specificity and/or sensitivity for the indicated species. The inclusion of antigenic peptides that exhibit cross-reactivity across *Babesia* species boundaries is also important with respect to the development of inclusive serological, or other immunologically-based assays, wherein the goal is to detect infection, not necessarily to identify a particular species responsible for infection. For example, the disclosure includes immunoassays wherein, in the context of a single test screen, multiple *Babesia* species are detectable.

Aspects of the present disclosure provide novel compositions and methods for diagnosing infection by one or more species of the *Babesia* genus. In some aspects, the instant disclosure provides compositions and methods for quickly, easily, and accurately distinguishing between infection by *B. microti* and *B. duncani*. The disclosure is based, in part, on the discovery of species-specific amino acid sequences encoding antigenic peptides (which may also be referred to in the art as peptide antigens or antigens), as described herein. Aspects of the present disclosure provide antigen-specific amino acid sequences for *Babesia* species, including *B. microti* and *B. duncani*. These novel amino acid sequences may be used in assays to identify infection by one or more species of the *Babesia* genus in samples from subjects suspected of having babesiosis, including but not limited to *Babesia* species comprising *B. microti*, *B. duncani*, B. MO1, *B. divergens*, *B. venatorum*, and *B. crassa*. With the amino acid sequences of the present disclosure, identification of *Babesia* infection in subject samples is performed with speed, sensitivity, and specificity at least equivalent to or greater than other current methods. The amino acid sequences of the present disclosure may be used in diagnostic and scientific assays. Non-limiting examples of suitable assays include immunoblots, line immunoblots, ELISA (enzyme-linked immunosorbent assay), etc. The amino acid sequences of the present disclosure may be used for the detection of *Babesia*-specific T-cells, for example, with the IgXSPOT test (IGeneX, Milpitas, CA).

In one aspect, a composition of the present disclosure comprises labelled and/or tagged and/or bound amino acid sequences, wherein the labelled and/or tagged and/or bound amino acid sequences comprise amino acid sequences SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19, and variants thereof which retain the immunological binding profile of the corresponding non-variant. In one aspect, a composition of the present disclosure comprises labelled and/or tagged and/or bound amino acid sequences, wherein the labelled and/or tagged and/or bound amino acid sequences comprise amino acid sequences having at least 90%, 95%, 98%, 99%, 99.5%, or 100% homology to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19, and variants thereof which retain the immunological binding profile of the corresponding non-variant. As used herein, a non-variant is an amino acid sequence with 100% sequence homology to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, or SEQ ID NO: 19. Variants of amino acid sequences SEQ ID NOs: 1-19 which retain the immunological binding profile of the corresponding non-variant may have conservative amino acid substitutions in conserved or non-conserved regions. The expression "variants" encompasses any modification(s) of a specified amino acid sequence (e.g., SEQ ID NOs: 1-19) which retain(s) the immunological binding profile of the corresponding non-variant. Such modifications may include insertions and deletions (internal or from the N- or C-terminus, or both). One skilled in the art, using no more than routine experimentation, could design and produce antigenic peptides carrying conservative amino acid substitutions in non-conserved regions, or even at non-conserved amino acid positions as identified by alignment comparisons. The term "immunological binding profile" as used herein refers to the ability of a labelled and/or tagged and/or bound amino acid sequence to be bound by antibodies present in a biological sample. Non-limiting examples of immunological binding profiles include FIGS. 2-4.

Sequences with less than 100% homology may be modified with one or more substitutions, deletions, insertions, or other modifications with respect to the amino acid sequences provided herein. Exemplary modifications include, but are not limited to conservative amino acid substitutions, which will produce molecules having functional characteristics similar to those of the molecule from which such modifications are made. Conservative amino acid substitutions are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution because both are similarly-sized negatively-charged amino acids. Groupings of amino acids by physico-chemical properties are known to those of skill in the art. The following groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). One of ordinary skill in the art can determine if sequences with less than 100% homology can bind naturally- or non-naturally-occurring *Babesia*-related antibodies, as well as the sensitivity and specificity of the antibody to the modified sequences. One of ordinary skill in the art will be able to identify sequences with significant homology to SEQ ID NOs: 1-19 of the present disclosure that give acceptable or equivalent responses in the methods of the present disclosure without undue experimentation, in view of the teachings of this specification.

Nucleic acid sequences, including polynucleotides and oligonucleotides, encoding the amino acid sequences of the present disclosure, and portions thereof, may be expressed in cultured cells to provide isolatable quantities of peptides displaying biological (e.g., immunological) properties of the antigenic peptide encoded by the amino acid sequences of the present disclosure. Because of redundancy of the genetic code, multiple nucleic acid sequences may be suitable for the production of the peptide sequences of the present disclosure. One of ordinary skill in the art will be able to determine one or more nucleic acid sequences for production of the amino acid sequences of the present disclosure. A nucleic acid sequence encoding an amino acid sequence of the present disclosure may be labeled by any suitable label known to one of ordinary skill in the art.

In this regard, nucleic acid sequences suitable for the production of the amino acid sequences of the present disclosure may be substantially homologous to naturally occurring sequences. Substantial homology of a nucleic acid sequence as used herein means that: (a) there is greater than 65%, 75%, 85%, 95%, 98%, or 99% homology with the naturally occurring sequence, or (b) the homologous nucleic acid sequence will hybridize to the compared sequence or its complementary strand under stringent conditions of the temperature and salt concentration. These stringent conditions will generally be a temperature greater than about 22° C., usually greater than about 30° C. and more usually greater than about 45° C., and a salt concentration generally less than about 1 M, usually less than about 500 mM, and preferably less than about 200 mM. The combination of temperature and salt concentration is more important in defining stringency than either the temperature or the salt concentration alone. Other conditions which affect stringency include GC content of the compared sequence, extent of complementarity of the sequences, and length of the sequences involved in the hybridization, as well as the composition of buffer solution(s) used in the hybridization mixture. These and other factors affecting stringency are well described in the scientific and patent literature. One of ordinary skill in the art will be able to determine suitable conditions for determining the homology of the nucleic acid sequences encoding the antigenic peptides of the present disclosure.

Homologous nucleic acid sequences may be determined based on the nature of a nucleotide substitution in the nucleic acid sequence. For example, synonymous nucleotide substitutions, that is, nucleotide changes within a nucleic acid sequence that do not alter the encoded amino acid sequence, will be better tolerated and, therefore, may be more numerous in a particular nucleic acid sequence than non-synonymous nucleotide substitutions. One of ordinary skill in the art will be able to determine the suitable number and location of substitutions that may be allowed in a nucleic acid sequence that encodes an amino acid sequence of the present disclosure without adversely affecting the antigenicity of the encoded antigenic peptide, without undue experimentation.

In another aspect, a composition of the present disclosure comprises labelled and/or tagged and/or bound amino acid sequences, wherein the labelled and/or tagged and/or bound amino acid sequences consist of amino acid sequences SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19, and/or variants thereof which retain the immunological binding profile of the corresponding non-variant. In some aspects, the composition comprises labelled and/or tagged and/or bound amino acid sequences, wherein the labelled and/or tagged and/or bound amino acid sequences consist of amino acid sequences SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19. As used herein, "consist of" or "consisting of", when used as a claim transition referring to an amino acid sequence, refers to amino acid sequences having 100% homology to the specified amino acid sequence (i.e., SEQ ID NOs: 1-19). With regard to the present disclosure, the phrase "wherein the labelled and/or tagged and/or bound amino acid sequences consist of" encompasses a composition having the one or more of the recited sequences and, for example, buffers, labels, etc. In other words, the sequence is limited to the sequence or sequences given but the composition is not limited. The definition specifically excludes amino acids naturally contiguous with a recited sequence being used as a label or tag, such as an oligonucleotide mass tag (OMT) for detection with mass spectrophotometry, as an element of the "composition comprising."

Labels and Tags

One or more amino acid sequences of the disclosure may be labelled and/or tagged and/or bound. In the context of the present disclosure, a "labelled" or "tagged" amino acid sequence is an amino acid sequence that is attached to a detectable moiety. As used herein, a "label" or "tag" is a detectable moiety that may be attached to an amino acid sequence of the disclosure. A label or tag may be covalently or non-covalently attached to an amino acid sequence of the disclosure. Non-limiting examples of such "tags" are natural and synthetic (i.e., non-naturally occurring) nucleic acid and amino acid sequences (e.g., poly-AAA tags), antibodies (covalently bound) and detectable moieties such as labels (discussed below). Thus, the definitions of the phrases "labelled" and "tagged" may have overlap in that a tag may also, in some instances, function as a label. Further, tags useful with the present disclosure may be linked to a label.

The amino acid sequences of the present disclosure, or any tags attached to an amino acid sequence of the present disclosure, may be labeled with any suitable label known to one of ordinary skill in the art. Such labels may include, but are not limited to, biotin/streptavidin (labeled), enzyme conjugates (e.g., horseradish peroxidase (HRP), alkaline phosphatase (AP), glucose oxidase and β-galactosidase), fluorescent moieties (e.g., FITC, fluorescein, rhodamine, etc.), biological fluorophores (e.g., green fluorescent protein, R-phycoerythrin) or other luminescent proteins, etc. Any suitable label known to one of ordinary skill in the art may be used with the present disclosure.

Further, in some aspects, the amino acid sequences of the present disclosure may be "bound." A "bound" amino acid sequence is an amino acid sequence that has been immobilized in order to permit the use of the amino acid sequence in a biological test such as, for example, immunoassays. In the context of the present disclosure, a "bound" amino acid sequence is an amino acid sequence attached (e.g., covalently or non-covalently bound, etc.) directly or indirectly to a non-natural surface or substance (i.e., a solid support). Further still, the "bound" amino acid sequences of the present disclosure may be attached, directly or indirectly, to a natural surface or substance (i.e., a solid support), either of which is not naturally associated with the amino acid sequence. Non-limiting examples of substances to which the amino acid sequences of the present disclosure may be bound are nitrocellulose, nylon, polyvinylidene difluoride (PVDF), plastics, metals, magnetic beads and agarose (e.g., beads). Linking agents known to those of ordinary skill in the art may be used to aid or enhance binding of the amino acid sequences of the present disclosure to a surface or substance.

Production of Amino Acid Sequences

In some aspects, amino acid sequences of the present disclosure may be natural occurring and isolated from a natural source. Further, in some aspects, amino acid sequences of the present disclosure may be non-natural, synthetic sequences, such as sequences produced by recombinant technology or sequences synthesized by protein synthesizing apparatuses. As such, amino acid sequences of the present disclosure may be isolated or may be produced by recombinant technology, as is described and enabled in the literature and in commonly referred to manuals such as, e.g., Short Protocols in Molecular Biology, Second Edition, F. M. Ausubel, Ed., all John Wiley & Sons, N.Y., edition as of 2008; and, Sambrook, et al., Molecular Cloning: A Laboratory Manual, 3rd ed., Cold Spring Harbor Laboratory Press, Cold Spring Harbor, 2001, and as is well known to one of ordinary skill in the art. In one aspect, amino acid sequences of the present disclosure are made recombinantly in E. coli.

As used herein, the term "vector" refers to a nucleic acid molecule capable of transporting between different genetic environments another nucleic acid to which it has been operatively linked. In addition to including a nucleic acid sequence encoding an amino acid sequence of the disclosure (e.g., SEQ ID NOs: 1-19) or variants thereof which retain the immunological binding profile of the corresponding non-variants, vectors of the present disclosure also include a heterologous nucleic acid sequence. As used herein, heterologous refers to a nucleic acid sequence that does not naturally occur in the organism from which the Markush group sequences are derived. The term "vector" may also refer to a virus or organism that is capable of transporting the nucleic acid molecule. One type of vector is a plasmid, a small, circular, double-stranded, extrachromosomal DNA molecule that is physically separate from and can self-replicate independently from chromosomal DNA. Some useful vectors are those capable of autonomous replication and/or expression of nucleic acids to which they are linked. Vectors capable of directing the expression of nucleic acids to which they are operatively linked are referred to herein as "expression vectors." Other useful vectors, include, but are not limited to bacterial plasmids and bacterial artificial chromosomes (BACs), cosmids, and viruses such as lentiviruses, retroviruses, adenoviruses, and phages.

Vectors useful in methods of the disclosure may include additional sequences including, but not limited to, one or more signal sequences and/or promoter sequences, or a combination thereof. Promoters that may be used in methods and vectors of the disclosure include, but are not limited to, cell-specific promoters or general promoters. Non-limiting examples of promoters that can be used in vectors of the disclosure are: ubiquitous promoters, such as, but not limited to: CMV, CAG, CBA, and EF1a promoters. Methods to select and use suitable promoters are well known in the art.

Vectors useful in methods of the disclosure may be used to express a fusion protein comprising sequences of the disclosure in a cell. Expression vectors and methods of their preparation and use are well known in the art. In some aspects of the disclosure, a nucleic acid sequence of an expression vector encodes a fusion protein comprising an amino acid sequence of the disclosure. It is well known in the art how to prepare and utilize fusion proteins that comprise a polypeptide sequence. In some aspects, a fusion protein comprising an amino acid sequence of the disclosure may also include an epitope tag that may be used for purification of the fusion protein or in a method of the disclosure. Non-limiting examples of epitope tags are a FLAG tag, a fluorescent tag (including but not limited to green fluorescent protein (GFP)), a GST tag, a hemagglutinin (HA), a poly-histidine (poly-His) tag, a Myc tag, an MBP tag, or a V5 tag. In some aspects, a fusion protein comprising an amino acid sequence of the disclosure may also include a detectable label, as described elsewhere herein.

Assays and Methods of Detection

Amino acid sequences of the present disclosure bind specifically to antibodies produced following infection by *Babesia* species. Specificity for said amino acid sequence, i.e., antibody specificity, is the property of antibodies which enables them to react preferentially with some antigenic determinants and not with others. Specificity is dependent on chemical composition, physical forces and molecular structure at the binding site. Sensitivity is how strongly the antibody binds to the antigenic determinant. One of ordinary skill in the art can easily determine specificity and sensitivity of an antibody for a particular amino acid sequence using standard affinity assays, such as immunoblotting, Ouchterlony assays, titer assays, etc.

In another aspect, the present disclosure provides methods of quickly and accurately detecting *Babesia* antibodies in a sample from a subject suspected of having babesiosis. Methods of the present disclosure for detecting *Babesia* antibodies in a sample from a subject suspected of having babesiosis, may comprise, for example, providing a biological sample (including but not limited to blood, saliva) obtained from a subject suspected of having babesiosis, mixing the biological sample with one or more of the labeled and/or bound amino acid sequences of the present disclosure and detecting a positive immunobinding reaction which indicates the presence of antibodies to one or more *Babesia* species in the sample. The antibodies may be detected by, for example, immunoblotting, Elispot, ELISA, Western blotting, lateral flow assay, or any other appropriate immunoassay known to one of ordinary skill in the art. These techniques are known to one of ordinary skill in the art and procedures can be found in common technical references. While similar, each of these techniques has its advantages and disadvantages. Other suitable techniques may be known to those of skill in the art and are incorporated herein.

To assess the impact of testing limitations and to determine levels of exposure to *Babesia* species, a modified Western blot procedure, the line immunoblot, was developed and employed in aspects of the disclosure described herein. A line immunoblot uses recombinant antigens from multiple *Babesia* species for serological identification and diagnosis of *Babesia* infection in serum from patients with suspected babesiosis. Infection with more than one *Babesia* species is possible and may occasionally be observed.

Western blotting can involve separating proteins by electrophoresis and then transferring to nitrocellulose or other solid media (e.g., polyvinylidene fluoride or PVDF-membrane and nylon membrane), and is described in more detail below. Immunoblotting can also involve applying proteins to a solid media manually or by machine. Preferably, the proteins or polypeptides are applied in straight lines or spots and dried, binding them to the solid support medium, e.g., nitrocellulose. The proteins used in an immunoblot can be isolated from biological samples or produced by recombinant technology, as is well known by those of ordinary skill in the art. The bound proteins are then exposed to a sample or samples suspected of having antibodies specific for the target proteins. With this procedure, a known antibody can be used to determine if a protein is present in a sample, such as when the proteins of lysed cells are separated by electrophoresis and transferred to the solid medium. Western blotting allows for the identification of proteins by size as well as by specificity for a specific antibody.

Similarly, with a procedure called immunoblotting, known proteins can be bound to the solid medium and samples, such as samples from subjects suspected of having an infection, can be tested for the presence of specific antibodies in the sample by contacting the bound protein with the sample. An antibody that binds the target protein is usually referred to as the primary antibody. A secondary antibody, specific for conserved regions of the primary antibody (for example, a rabbit-anti-human IgG antibody may be used to detect primary human antibodies) is used to detect any bound primary antibodies. The secondary antibody is usually labeled with a detectable moiety for visualization. Non-limiting examples of suitable labels include, for example, chromophores such as biotin, radioactive moieties and enzymes such as alkaline phosphatase, etc. The use of these and other materials for the visualization of antibodies are well known to one of ordinary skill in the art.

The Enzyme-Linked ImmunoSpot (ELISPOT) method can detect human T cells that respond to *Babesia*-specific antigens in vitro. In an ELISPOT assay, the surfaces of PVDF membrane in a 96-well microtiter plate are coated with capture antibody that binds, for example, anti-Interferon gamma (IFNγ) or other cytokine-specific antibody. During the cell incubation and stimulation step, the T cells isolated from patient whole blood are seeded into the wells of the plate along with aforementioned sequence(s), and form substantially a monolayer on the membrane surface of the well. Upon stimulation of any antigen-specific cells with one or more of the sequences of the present disclosure they are activated and they release the IFNγ, which is captured directly on the membrane surface by the immobilized antibody. The IFNγ is thus "captured" in the area directly surrounding the secreting cell, before it has a chance to diffuse into the culture media, or to be degraded by proteases and bound by receptors on bystander cells. Subsequent detection steps visualize the immobilized IFNγ as an ImmunoSpot; essentially the secretory footprint of the activated cell.

For a specific example of an ELISPOT test, each well of the plate is coated with a purified cytokine-specific antibody specific for the test or cell being detected. Subject's (i.e., a subject suspected of having babesiosis) T cells are isolated and cultured in each well and stimulated with recombinant antigens of one or more sequences of the present disclosure. *Babesia*-positive patient cells secrete cytokine in response to stimuli, which is captured by the antibody coated in the well and further detected by ELISA.

ELISA assays are also used to detect antigens. The ELISA assay can permit the quantification of a specific protein in a mix of proteins (for example, a lysate) or determine if a peptide is present in a sample. Likewise, ELISA assays can be used to determine if a specific antibody is present by using a specific antigen as a target. As used with the present disclosure, target amino acid sequence(s) are attached to a surface. Then, if present in the sample being tested, the reactive antibody can bind to the antigen. A secondary antibody linked to an enzyme is added, and, in the final step, a substance containing the enzyme's substrate is added. The subsequent reaction produces a detectable signal, most commonly a color change in the substrate.

Lateral flow assays, also referred to by a variety of other names that include but are not limited to lateral flow tests, lateral flow devices, lateral flow immunoassays, lateral flow immunochromatographic assays, and rapid tests, are simple, versatile, paper-based platforms for detecting and/or quantifying the presence of one or more analytes, such as an antigen, in a mixture, such as a liquid sample. Lateral flow assays may be qualitative or quantitative. In a lateral flow assay, a sample containing one or more analytes of interest is applied to an adsorbent sample pad and is drawn via capillary action through various zones of polymeric test strips to which are attached molecules that can interact with the analyte(s). The sample migrates to the conjugate release pad, which contains molecules that specifically bind to the analyte(s) of interest and are conjugated to fluorescent, colored, or otherwise detectable particles. Finally, the sample, including the bound analyte(s) migrates into the detection zone. Within the porous membrane of the detection zone are biological components such as antibodies or antigens, that are immobilized in lines and that will react with the detectable particles. Lateral flow assays typically have a control line for confirming sample flow through the strip and one or more test lines for detecting the presence of the analyte(s) of interest. The results may be read by eye or with a machine capable of reading and interpreting the results. A lateral flow assay may be designed as a direct or "sandwich" assay, in which the presence of a colored line at the test line position indicates a positive test, or as a competitive assay, in which the absence of a colored line indicates a positive test. Direct and competitive assays may be multiplexed.

In aspects of methods of the present disclosure, a positive result for infection by one or more *Babesia* species, if present in a biological sample obtained from a subject suspected of having a *Babesia* infection, is indicated when a biological sample obtained from a subject suspected of having a *Babesia* infection is provided and contacted with a composition of the disclosure comprising labelled and/or tagged and/or bound amino acid sequences, wherein the labelled and/or tagged and/or bound amino acid sequences comprise amino acid sequences SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19, and variants thereof which retain the immunological binding profile of the corresponding non-variant under conditions appropriate for specific antibody binding to an epitope, and specific binding of IgM- and/or IgG-class antibodies, if present in the biological sample, with amino acid sequences included in the composition is detected, wherein the sample is scored as positive for infection by one or more *Babesia* species when (i) a positive immunobinding reaction with IgM-class antibodies is detected for at least two of SEQ ID NOs: 1-19, or (ii) a positive immunobinding reaction with IgG-class antibodies is detected for at least two of SEQ ID NOs: 1-19, and wherein a positive score for infection indicates infection by one or more *Babesia* species in the subject.

In methods of the present disclosure, any primary antibody bound to a peptide encoded by an amino acid sequence of the present disclosure may be detected with anti-human antibodies, such as IgG or IgM, used as the secondary antibody conjugated to a detectable moiety. As discussed elsewhere herein, the detectable moiety may be selected from the group consisting of chromophores, radioactivity moieties and enzymes or other detectable moiety known to one of ordinary skill in the art. In one aspect, the detectable moiety comprises alkaline phosphatase. In another aspect the detectable moiety comprises biotin. In one aspect, the *Babesia* genus comprises species selected from *B. microti*, *B. duncani*, B. MO1, *B. divergens*, *B. venatorum*, and *B. crassa*.

In another aspect of the present disclosure, methods are provided for detecting and distinguishing infection by *B. microti* and/or *B. duncani* in a biological sample. The sample may be from a subject suspected of having babesiosis. In one aspect of methods of the disclosure, a positive result for infection by *B. microti* or *B. duncani* is indicated when a biological sample obtained from a subject suspect of having a *Babesia* infection is provided and contacted with a composition of the disclosure under conditions appropriate for specific antibody binding to an epitope, wherein the composition comprises labelled and/or tagged and/or bound amino acid sequences, wherein the labelled and/or tagged and/or bound amino acid sequences comprise amino acid sequences SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19, and variants thereof which retain the immunological binding profile of the corresponding non-variant, and detecting specific binding of IgM- and/or IgG-class antibodies, if present in the biological sample, with the amino acid sequences of the composition. In one aspect of methods of the disclosure, a sample is scored as positive for infection by *B. microti* when a positive immunobinding reaction with IgM- or IgG-class antibodies is detected for at least one of SEQ ID NOs: 1-7, 9, 11, or 13 and at least one of SEQ ID NOs: 8, 10, or 12, and wherein a positive score indicates infection by *B. microti*. In another aspect of methods of the disclosure, a sample is scored as positive for infection by *B. duncani* when a positive immunobinding reaction with IgM- or IgG-class antibodies is detected for at least one of SEQ ID NOs: 1-7, 9, 11, 13, or 16-19 and at least one of SEQ ID NOs: 14 or 15, and wherein a positive score indicates infection by *B. duncani*. Amino acids may be labeled to confirm their presence if positive results are not obtained in the assay.

Subjects and Cells

As used herein, a subject may be an animal, such as a mammal or a non-mammal. Non-limiting examples of mammalian subjects include primates (including but not limited to humans), rodents (including but not limited to mice, rats, squirrels, chipmunks, prairie dogs), lagomorphs, deer, canids (including but not limited to dogs, foxes, coyotes, and wolves), felids (including but not limited to domestic cats, bobcats, cougars, and other wild cats), bears, horses, cows, sheep, goats, and pigs. Non-limiting examples of non-mammalian subjects include birds, amphibians, lizards, insects, and arthropods. As used herein, a cell may be a bacterial cell, including but not limited to *E. coli*, or an animal cell, either mammalian or non-mammalian.

EXEMPLIFICATION

Example 1. Detection of *Babesia* Infection in Patient Samples

Methods

Patient Serum Samples and Rabbit Antisera

Patient sera used were leftover decoded patient sera received for tick-borne testing at IGeneX (IGeneX, Milpitas, CA) that would otherwise have been discarded. Rabbit antiserum to *B. microti* and *B. duncani* recombinant proteins was raised using *B. microti* recombinant proteins and *B. duncani* recombinant proteins, according to standard methods known in the art.

Preparation of Recombinant Antigens and ImmunoBlots

Using recombinant antigens from several species of *Babesia*, simple and rapid immunoblot (IB) assays were developed for detection of *Babesia*-specific IgM and IgG antibodies in a patient's serum in order to provide a laboratory diagnosis of *Babesia*. Briefly, several *Babesia* genus-specific and species-specific antigens were identified. Recombinant proteins for all 19 identified antigens (SEQ ID NOs: 1-19) were prepared by cloning portions of the selected genes into pET vectors, expressing the proteins in *Escherichia coli*, and purifying the proteins by metal affinity chromatography followed by gel filtration as previously described [Liu et al., *Healthcare* 6, 99 (2018)]. All proteins used for IB were >90% pure by Coomassie blue staining after SDS PAGE. The *Babesia* antigens and control proteins were sprayed in straight lines to yield 7-19 ng of protein as a line in each 3 mm strip onto nitrocellulose membrane as previously described [Liu et al., *Healthcare* 6, 99 (2018)]. The two control proteins were Protein L (Sigma) for detecting the addition of human serum and a mixture of human IgM and IgG for detecting the addition of alkaline phosphatase conjugated anti-human antibodies as previously described [Liu et al., *Healthcare* 6, 99 (2018)]. The membranes were then blocked with 5% non-fat dry milk and sliced into 3 mm wide strips (TB strip). Table 1 lists IB bands and corresponding SEQ ID NOs.

TABLE 1

| ImmunoBlot bands and corresponding SEQ ID NOs | | |
|---|---|---|
| Protein band # | SEQ ID NO: | |
| | | *Babesia microti* protein |
| 1 | 1 | Bm8630 |
| 2 | 2 | Bm5294 |
| 3 | 3 | Bm4855 |
| 4 | 4 | Bm0985 |
| 5 | 5 | Bm1510 |
| 6 | 6 | Bm0320 |
| 7 | 7 | Bm9435 |
| 8 | 8 | Bm2975 |
| 9 | 9 | Bm3280 |
| 10 | 10 | Bm3430 |
| 11 | 11 | Bm0690 |
| 12 | 12 | BMGP112 |
| 13 | 13 | BMIPA48 |
| | | *Babesia duncani* protein |
| 14 | 14 | BdGPI6 |
| 15 | 15 | BdGPI8 |
| 16 | 16 | BdGPI17 |
| 17 | 17 | BdHSP-70-1 |
| 18 | 18 | BdHSP-70-2 |
| 19 | 19 | BdHSP-70-3 |

ImmunoBlotting

Prior to use, each strip was labeled and then soaked in 1 mL of diluent (100 mm Tris, 0.9% NaCl, 0.1% Tween-20 and 1% non-fat dry milk) for 5 min in a trough. A 10 µL aliquot of the test or control serum was added to a corresponding TB strip in a trough. The strips were then incubated at room temperature for one hour with serum, followed by three washes with wash buffer at ambient temperature. After aspirating the final wash solution, strips for detecting IgG and IgM were incubated with alkaline phosphatase-conjugated goat anti-human IgG at 1:10,000 dilution and IgM at 1:3000 dilution, respectively, for one hour. After three washes, bands were visualized by reaction with 5-bromo-4-chloro-3-indolylphosphatenitro-blue tetrazolium or BCIP/NBT. The reactions were terminated by washing with distilled water when a calibration control used in parallel produced a visible band. *Babesia* D3 strips were also reacted in parallel with a mixture of human sera from patients with confirmed *Babesia* infection as a positive control and sera from uninfected persons as a negative control.

Reading IB Strips and Result Interpretation

For a run to be considered acceptable for scoring, all bands were required to show up on the positive control strip and the negative control strip was required to show only the C1 and C2 control bands. All bands were recorded for each sample. A sample was considered positive for the *Babesia* genus if at least two of the 19 bands were present on the IB, as detected by either IgM or IgG. A sample was considered *B. microti*-positive if at least one of bands 1-7, 9, 11, and 13, and at least one of bands 8, 10, and 12 were present on the IB (either IgM or IgG). A sample was considered *B. duncani*-positive if at least one of bands 1-7, 9, 11, 13, 16-19, and at least one of bands 14 and 15 were present on the IB (either IgM or IgG).

RESULTS AND CONCLUSION

*Babesia* IB strips were tested with serum samples from patients positive for *Babesia* by FISH and/or IFA, as well as other tick-borne diseases and *E. coli* antibodies. These results demonstrated that the *Babesia* IB could detect *Babesia* infection at the genus level and could speciate to *B. microti* and *B. duncani* in a single test. *Babesia* IB blots did not cross react with antibodies to other tick-borne infections (100% specificity to *Babesia*) as shown in FIG. 1 and Table 2.

TABLE 2

| Lack of cross-reactivity with antibodies to non-*Babesia* tick-borne infections | |
|---|---|
| Antibodies to: | *Babesia* IB |
| *Babesia* | |
| *Babesia microti* | Positive |
| *Babesia duncani* | Positive |
| Tick -Borne Relapsing Fever *Borrelia* | |
| *B. hermsii* | Negative |
| *B. tucica* | Negative |
| *B. coriaceae* | Negative |
| *B. miyamotoi* | Negative |
| *Borrelia burgdorferi* | Negative |
| *Borrelia burgdorferi* B31 | Negative |
| *Borrelia burgdorferi* 297 | Negative |
| *Bartonella* | |
| *B. elizabethae* | Negative |
| *B. henseale* | Negative |
| *B. quintana* | Negative |
| *B. vinsonii* | Negative |
| *Echerichia coli* | Negative |
| *Ehrlichia chaffenssis* | Negative |
| *Anaplasma phagocytophia* | Negative |
| *Rickettessia* | Negative |

Figure 2:
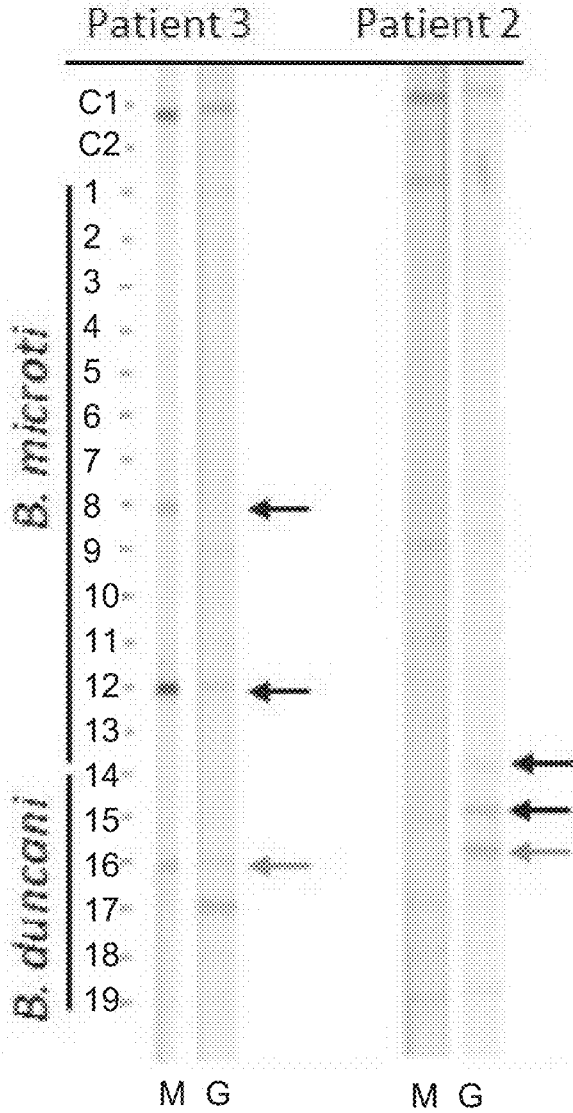
FIG. 2 presents photomicrographic images showing *Babesia*-positive patient sera tested with *Babesia* Immuno-Blots (IBs). Patient 3 was positive for *B. microti* and Patient 2 was positive for *B. duncani* by immunofluorescence assay (IFA) and western blots. *Babesia* D3 testing confirmed sera from both patients were positive for *Babesia* infection at the genus level. Serum from Patient 3 was positive for *B. microti*; serum from Patient 2 was positive for *B. duncani.* Arrows indicate bands 8, 12, and 14-16 (SEQ ID NOs: 8, 12, and 14-16, respectively). M, IgM; g, IgG.
Figure 3:
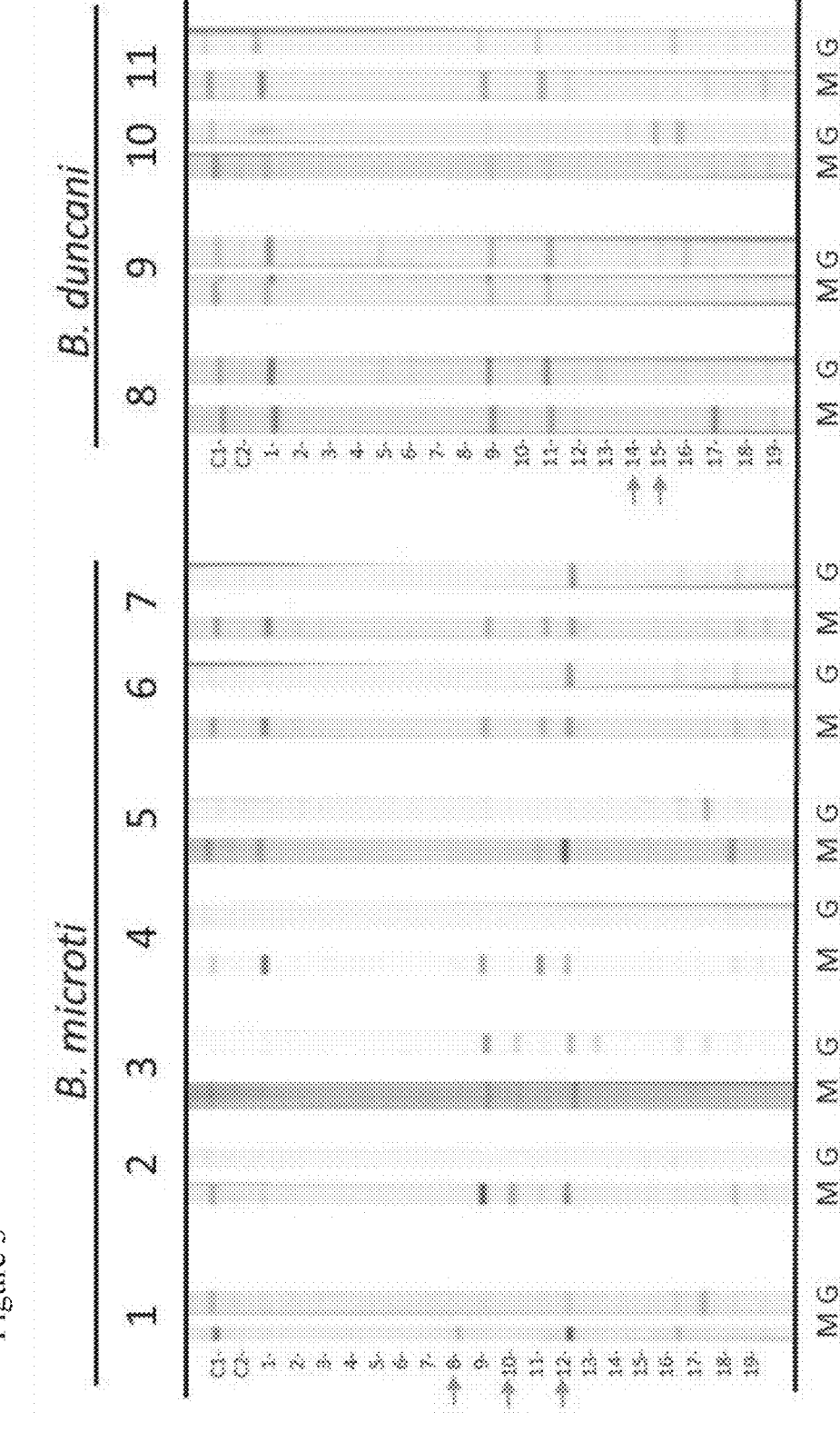
FIG. 3 presents photomicrographic images showing patient serum samples (1-11) tested with *Babesia* IgM (M) and IgG (G) ImmunoBlots. Bands 1-7, 9, 11, 13, 16-19 were *Babesia* genus-specific (SEQ ID NOs: 1-7, 9, 11, 13, and 16-19, respectively). Bands 8, 10, and 12 (SEQ ID NOs: 8, 10, and 12, respectively) were specific for *B. microti,* indicated by arrows for samples 1-7. Bands 14 and 15 (SEQ ID NOs: 14 and 15, respectively) were specific for *B. duncani,* indicated by arrows for samples 8-11. Samples 1-7 were positive for *B. microti*; samples 8-11 were positive for *B. duncani.*

As shown in FIGS. 2 and 3, the *Babesia* IB detected both *B. microti* and *B. duncani*. A set of 37 serum samples from patients suspected of babesiosis were tested. Twenty-eight samples were identified as positive for *Babesia* using the *Babesia* IB. Results are summarized in Table 3 and detailed results shown in FIG. 4.

TABLE 3

| Test | n | Summary of Babesia IB performance in clinical samples BM IFA | | | | BD IFA | | | BM-BD | NEG |
|------|---|---------|---|-------|------|--------|-------|-------|-------|-----|
| | | FISH(+) | | | | | | | | |
| | 19 | 10 | 5 | | | 4 | | | 2 | 10 |
| IB | 19 | 10 | 5 | 1 Neg | | 4 | | | 2 | 10 |
| | | FISH (−) | | | | | | | | |
| | n | 18 | 5 | | | 13 | | | 0 | 0 |
| IB | 18 | 13 | 4 | 1 Neg | 3 BD | 4 GENUS | 4 Neg | | 0 | 0 |
| Total | 28 | 23 | 9 | 1 Neg | | 7 | 4 | 4 Neg | 2 | 0 |
| Sensitivity | | | | | | 82.1% | | | | |
| Specificity | | | | | | 100% | | | | |

Based on these data, *Babesia* IB sensitivity was 82.1%. Thus, the *Babesia* IB could be used to detect *Babesia* infection generally (genus-level detection), and to distinguish between infection by *B. microti* and *B. duncani*. It had 100% specificity as shown in FIG. 1 and Table 2.

EQUIVALENTS

Although several aspects of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific aspects of the disclosure described herein. It is, therefore, to be understood that the foregoing aspects are presented by way of example only and that, within the scope of the appended claims and equivalents thereto; the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated by reference in their entirety herein.

What is claimed is:

1. A composition comprising labelled and/or tagged and/or bound amino acid sequences SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19.

2. The composition of claim 1, wherein the bound amino acid sequences are bound to a solid support selected from the group consisting of nitrocellulose, nylon, polyvinylidene difluoride (PVDF), plastic, metal, magnetic beads, and agarose.

3. A method for detecting infection by one or more Babesia species, if present in a biological sample obtained from a subject suspected of having a Babesia infection, the method comprising:
   (a) providing the composition of claim 1;
   (b) providing the biological sample obtained from the subject suspected of having a Babesia infection;
   (c) contacting the biological sample with the composition under conditions appropriate for specific antibody binding to an epitope; and
   (d) detecting specific binding of IgM- and/or IgG-class antibodies, if present in the biological sample, with the amino acid sequences of the composition, wherein the biological sample is scored as positive for infection by one or more Babesia species when:
      (i) a positive immunobinding reaction with IgM-class antibodies is detected for at least two of the amino acid sequences of the composition, or
      (ii) a positive immunobinding reaction with IgG-class antibodies is detected for at least two of the amino acid sequences of the composition,
   and wherein a positive score for infection indicates infection by one or more Babesia species in the subject.

4. The method of claim 3 wherein the binding of IgM-class antibodies is detected through the use of an anti-human IgM antibody linked to a detectable moiety.

5. The method of claim 3 wherein the binding of IgG-class antibodies is detected through the use of an anti-human IgG antibody linked to a detectable moiety.

6. The method of claim 5, wherein the detectable moiety is selected from the group consisting of chromophores, radioactive moieties, and enzymes.

7. The method of claim 6, wherein the detectable moiety comprises alkaline phosphatase.

8. The method of claim 6, wherein the detectable moiety comprises biotin.

9. The method of claim 3, wherein the one or more Babesia species comprise one or more of B. microti, B. duncani, B. MO1, B. divergens, B. venatorum, and B. crassa.

10. A method for detecting species-specific infection by B. microti and/or B. duncani, if present in a biological sample obtained from a subject suspected of having a Babesia infection, the method comprising:
   (a) providing the composition of claim 1;
   (b) providing the biological sample obtained from the subject suspected of having a Babesia infection;
   (c) contacting the biological sample with the composition under conditions appropriate for specific antibody binding to an epitope; and
   (d) detecting specific binding of IgM- and/or IgG-class antibodies, if present in the biological sample, with the amino acid sequences of the composition, wherein:
      (i) the biological sample is scored as positive for infection by B. microti when a positive immunobinding reaction with IgM- or IgG-class antibodies is detected for at least one of SEQ ID NOs: 1-7, 9, 11, and 13 and at least one of SEQ ID NOs: 8, 10, and 12, or
      (ii) the biological sample is scored as positive for infection by B. duncani when a positive immunobinding reaction with IgM- or IgG-class antibodies is detected for at least one of SEQ ID NOs: 1-7, 9, 11, 13, and 16-19 and at least one of SEQ ID NOs: 14 and 15,
   and wherein a positive score indicates infection by B. microti and/or B. duncani.

11. The method of claim 10 wherein the binding of IgM-class antibodies is detected through the use of an anti-human IgM antibody linked to a detectable moiety.

12. The method of claim 10 wherein the binding of IgG-class antibodies is detected through the use of an anti-human IgG antibody linked to a detectable moiety.

13. The method of claim 12, wherein the detectable moiety is selected from the group consisting of chromophores, radioactive moieties, and enzymes.

14. The method of claim 13, wherein the detectable moiety comprises alkaline phosphatase.

15. The method of claim 13, wherein the detectable moiety comprises biotin.

16. A vector comprising nucleic acid sequences coding for amino acid sequences SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19.

* * * * *

SEQUENCE LISTING

```
<160> NUMBER OF SEQ ID NOS: 19

<210> SEQ ID NO 1
<211> LENGTH: 790
<212> TYPE: PRT
<213> ORGANISM: Babesia microti Bm8630

<400> SEQUENCE: 1

Met His Asn Ser Asn Ile Phe Arg Ile Gly Ile Leu Tyr Thr Leu Gly
1               5                   10                  15

Leu Ile Ile Ile Asn Gly Pro Ile Ile Val Ser Ala Asn Thr Pro Gln
            20                  25                  30

Lys Val Asn Glu Gln Lys Asn Asp Tyr Phe Tyr Val Asp Gly Val Lys
        35                  40                  45

Tyr Arg Asn Pro Ser Asn Glu His Pro Ala Cys Arg Gly Asn Val Asp
    50                  55                  60

Leu Val Ile Ile Val Lys Trp Pro Gly Gly Leu Asp Lys Tyr Ser Trp
```

```
65                70                75                80

Ser Glu Lys Ile Ala Glu Tyr Leu Pro Lys Phe Val Ser Gln Leu Glu
                    85                90                95

Ile Ser Glu Asn Arg Phe Arg Val Gly Leu Ile Met Ser His Thr Tyr
            100               105               110

Asp Lys Asp Phe Leu Val Asp Leu Asn Gly Glu His Ser Leu Asp Lys
        115               120               125

Thr Lys Leu Leu Glu Glu Val Glu Lys Ser Val Asn Val Ser Asn Phe
    130               135               140

Val Ile Gly Thr Lys Leu Glu Lys Met Leu Asn Val Ala Tyr Leu Met
145               150               155               160

Phe Lys Lys Ser Lys Arg Leu Asn Thr Val Lys Met Ile Tyr Leu Ile
                165               170               175

Ser Asp Gly Met Tyr Ile Ser Asp Glu Glu Val Glu Lys Val Leu Asn
            180               185               190

Lys Val Arg Ala Tyr Pro Ile Gln Val Tyr Val Gln Gly Ile Gly Glu
        195               200               205

Thr Ser Lys Leu Trp Leu Lys Pro His Met Gly Cys Thr Leu Asp Asn
    210               215               220

Ser Tyr Pro Cys Pro Asn Phe Met Tyr Ser Lys Ile Asp Glu Pro Leu
225               230               235               240

Glu Pro Lys Asp Ala Tyr Thr Arg Met Cys Leu Gly Met Pro Gln Asn
                245               250               255

Ala Val Cys Phe Ile Gln Tyr Gly Glu Phe Asn Ser Cys Lys Leu Pro
            260               265               270

Cys Ser Pro Tyr Ser Val Lys Ser Ala Leu Ala Thr Ser Tyr Thr Thr
        275               280               285

Leu Arg Gly Pro Thr Phe Gly Tyr Val Gly Phe Lys Pro Gly Val Asp
    290               295               300

Cys Lys Met Gln Ala His Phe Lys Asp Met Lys Phe Lys Lys Cys Thr
305               310               315               320

Leu Lys Asp Cys Met Thr Asp Glu Glu Tyr Ala Glu Tyr Leu Asn Asn
            325               330               335

Lys Lys Lys Asn Asn Arg Ile Asp Ile Lys Asn Ala Val Thr Pro Ile
            340               345               350

Met Asp Lys Asp Lys Gly Ser Lys Ser Thr Ile Asp Glu Lys Ser Pro
        355               360               365

Thr Gly Glu Glu Thr Asp Thr Ser Asp Lys Ser Gln Thr Glu Thr Gly
    370               375               380

Glu Thr Val Glu Glu Ile Asp Glu Thr Ile Thr Asp Gly Thr Glu Glu
385               390               395               400

Thr Asp Thr Ser Asp Lys Ser Gln Thr Glu Thr Gly Glu Thr Val Glu
                405               410               415

Glu Ile Asp Glu Thr Ile Thr Asp Gly Thr Glu Glu Thr Asp Thr Ser
            420               425               430

Asp Lys Ser Gln Thr Glu Thr Gly Glu Thr Val Glu Glu Ile Asp Glu
        435               440               445

Thr Ile Thr Asp Gly Thr Glu Glu Thr Asp Thr Ser Asp Lys Ser Gln
    450               455               460

Ala Glu Thr Gly Lys Thr Val Glu Thr Thr Asn Asn Thr Ser Asp
465               470               475               480

Thr Ile Asn Thr Ser Gly Gly Thr Asp Lys Ser Gln Ala Glu Thr Gly
            485               490               495
```

-continued

```
Lys Thr Val Glu Thr Thr Thr Asn Asn Thr Ser Asp Thr Ile Asn Thr
            500                 505                 510

Ser Gly Gly Thr Asp Lys Ser Gln Thr Glu Thr Gly Lys Thr Val Glu
            515                 520                 525

Thr Thr Thr Asn Asn Thr Ser Asp Thr Ile Asn Thr Ser Gly Gly Thr
            530                 535                 540

Asp Lys Ser Gln Ala Glu Thr Gly Lys Thr Val Glu Thr Thr Thr Asn
545                 550                 555                 560

Asn Thr Ser Asp Thr Ile Asn Thr Ser Gly Gly Thr Asp Lys Ile Gly
                565                 570                 575

Pro Asn His Pro Ile Asn Asn Asn Thr Phe Lys Thr Pro Ile His Lys
            580                 585                 590

Val Asp His Lys Ser Pro Glu Asn Val Glu Glu Ser Lys Glu Lys His
            595                 600                 605

Glu Ala Asn Lys His Ala Asp Ser Thr Lys Asp Thr Asn Gly Glu Asn
            610                 615                 620

Lys Gly Asn Glu Ser Lys Asn Lys Phe Leu Ser Thr Ala Asn Lys Val
625                 630                 635                 640

Lys Asn Ala Leu Phe Tyr Thr Ala Asn Thr Arg Lys Leu Val Ser Asp
                645                 650                 655

Lys Pro Glu Thr Ile Glu Ser Asn Val Ser Val Lys Ser Thr Asn His
            660                 665                 670

Ser Asn Lys Asn Val Ala Gly Asp Asn Asn Ser Asn Pro Lys His Asn
            675                 680                 685

Asn Ala Asp Glu Val Ile Lys Ile Asn Asn Gly His Ser Glu Ala His
            690                 695                 700

Thr Asp Asp Phe Glu Ser Ser Asn Asp Val His Thr Met Ser Ile Gly
705                 710                 715                 720

Asn Gln Asn Val Lys Ile Ala Gly Gly Val Val Gly Gly Val Val Ile
                725                 730                 735

Phe Gly Leu Val Ala Leu Ala Phe Ala Asn Lys Arg Lys Gln Ser Thr
                740                 745                 750

Gly Tyr Gly Tyr Thr Gly Leu Val Tyr Gly Asp Glu Asp Asp Glu Ile
            755                 760                 765

Lys Tyr Asp Glu Asn Pro Glu Glu Phe Thr Val Thr Gly Ile Asp Asp
            770                 775                 780

Ala Leu Trp Gly Glu Lys
785                 790

<210> SEQ ID NO 2
<211> LENGTH: 596
<212> TYPE: PRT
<213> ORGANISM: Babesia microti Bm5294

<400> SEQUENCE: 2

Met Met Lys Phe Leu His Ile Thr Val Ile Thr Phe Leu Tyr Leu Leu
1               5                   10                  15

Asn Val Tyr Leu Ile Ser Gly His Asn Ile Leu Gly Asn Ile Pro Asp
            20                  25                  30

Lys Lys Thr Phe Arg Glu Glu Gln Asp Val Leu Lys Ser Ala Leu Glu
            35                  40                  45

Asp Gly Met Val Ile Leu Phe Glu Ser Glu Phe Ile Ser Arg Ala Arg
            50                  55                  60

Pro Ala Ser Asp Asn Ser Ala Thr Asn Asp Asn Leu Ser Ser Glu Glu
```

```
65                    70                    75                    80

His Ser Asn Asp Asn Asn Leu Glu Lys Ile Asp Asp Lys Lys Arg Asn
                85                    90                    95

Glu Leu Arg Lys Asp Ala Lys Val Met Ser Glu Val Ile Leu Lys Arg
            100                   105                   110

Arg Glu Gly Glu Leu Ser Thr Ile Pro Lys Lys Asp Gly Thr Leu His
            115                   120                   125

Ile Met Trp Lys Leu Ile Phe Tyr Ile Leu Tyr Ser Arg Ser Gly Lys
        130                   135                   140

Trp Leu Phe Asn Asn Pro Ser Asp Met Asn Leu Lys Asp Ala Lys Pro
145                   150                   155                   160

Gly His His Lys Val Leu Lys Ser Thr Pro Ala His Ile Asp Asn Asn
                165                   170                   175

Ile Pro Leu Pro Glu Gln Gln Ile Tyr Ser Ile Ser Asn Ile Pro Glu
            180                   185                   190

Val Leu Pro Glu Lys Asn Gly Lys Thr Pro Ile Leu Leu Phe Gly Met
            195                   200                   205

Glu Ala Phe Val Ile Phe His Leu Ile Asn Gln Ala Met Leu Glu Ile
        210                   215                   220

Val Asn Ser Ser Asp Pro Ile Glu Glu Lys Val Leu Phe Ser Glu Gln
225                   230                   235                   240

Trp Val His Phe Val Lys His His Phe Phe Ile Phe Phe Pro Tyr Asn
                245                   250                   255

Ala Ile Thr Ser Lys Arg Cys Val Arg Leu Leu Ser Asp Asn Thr Leu
            260                   265                   270

Glu Ser Glu Met Glu Leu Leu Asp Val Cys Lys Ser Leu Ala Glu Lys
        275                   280                   285

Ser Glu Lys Ser Asp Leu Leu Glu Thr Phe Ile Met Ile Asp Pro Glu
        290                   295                   300

Asn Asn Gly Asp Leu Leu Glu Lys Cys Ile Asn Glu Lys His Ile Ile
305                   310                   315                   320

Pro Ser Tyr Met Lys Leu Asn His Glu Lys Leu Ser His Leu His Leu
            325                   330                   335

Lys His Asn Leu Ala Met Glu Leu Ser Asp Phe Ile Ser Thr Tyr Gly
            340                   345                   350

Met Ile Met Thr Asn Ala Glu Gln Glu Ile Phe Lys Asp Asn Asn Ile
        355                   360                   365

Leu Asn Ser Lys Phe Trp Gly Ala Lys Cys Thr Lys Asp Glu Ala Ile
        370                   375                   380

Lys Ala Glu Asn Glu Ile Ile Lys Leu Phe Ser Asn Ile Gln Lys Asp
385                   390                   395                   400

Leu Asn Gly Val Ile Thr Lys Thr Phe Gln Lys Leu Leu Asp Leu Leu
                405                   410                   415

Glu Lys Asn Gly Gly Asn Ile Lys Ser Gly Pro Ala Lys Ser Leu Ile
            420                   425                   430

Lys Ala Glu Asn Asn Glu Phe Gln Ala Ala Lys Lys Glu Cys Glu Ser
        435                   440                   445

Asn Asn Glu Leu Lys Lys Asn Ile Glu Glu Ala Lys Thr Gln Phe Leu
        450                   455                   460

Lys Tyr Ala Ala Asp Gly Ser Ser Gly Gly Glu Glu Leu Val Lys Glu
465                   470                   475                   480

Leu Ala Asn Asn Glu Leu Ser Glu Trp Lys Phe Asn Val Ser Ala His
                485                   490                   495
```

-continued

```
Ile Leu Asp Thr Met Asn Lys Thr Cys Glu Glu Asp Ser Ala Phe Cys
            500                 505                 510

Leu Ser Ala Ile Lys His Cys Arg Lys Ser Leu Glu Gly Leu Glu Ser
            515                 520                 525

Asp Thr Glu Gln Tyr Lys Ile Ile Glu Lys Leu His Arg Ala Leu Ser
            530                 535                 540

Ala Ala Leu Leu Lys Ser Gly Lys Leu Asn Glu Lys Asp Tyr Ile Glu
545                 550                 555                 560

Glu Leu Ser Gly Tyr Ile Lys His Asp Gln Asn Glu Leu Ser Thr Asp
                565                 570                 575

Lys Pro Gln Gln Ser Ser Met Leu Gln Ile Arg Met Ala Arg Ile Arg
            580                 585                 590

Arg His Lys Ile
        595

<210> SEQ ID NO 3
<211> LENGTH: 271
<212> TYPE: PRT
<213> ORGANISM: Babesia microti Bm4855

<400> SEQUENCE: 3

Met Thr Val Thr Thr Ile Ala Leu Thr Val Ser Ile Val Ser Tyr Ile
1               5                   10                  15

His Gly Ser Pro Ser Asn Gly Leu Tyr Glu Ser Asn Leu Phe Tyr Thr
            20                  25                  30

Glu Gly Tyr Gly Lys Tyr Leu Thr Ser Pro Thr Lys Ile Lys Thr Ile
            35                  40                  45

Glu Phe Gly Gly Tyr Lys Phe Glu Phe Asp Asp Asp Thr Leu Pro Val
            50                  55                  60

Thr Ser Ile Thr Lys Ile Asp Val Ile Thr Tyr Asp Asp Lys Pro Ile
65                  70                  75                  80

Leu Phe Glu Phe Ile Ser Asp Lys Asp Arg Pro Tyr Arg Arg Phe Tyr
                85                  90                  95

Tyr Tyr Thr Leu Asp Ser Lys Thr Asn Lys Leu Tyr Asn Tyr Val Thr
            100                 105                 110

Ala Glu Thr Gly Tyr Asn Val Glu Asp Ser Ser Gly Leu Lys Tyr Tyr
            115                 120                 125

Thr Glu Leu Ser Lys Ser Gly Ile Asn Asp Val Leu Gln Asp Leu Asp
            130                 135                 140

Lys Asn Ile Asp Glu Ser Asn Ile Glu His Leu Lys Thr Ser Tyr Val
145                 150                 155                 160

Thr Lys Gly Leu Asn Ile Ala Ile Glu Val Tyr Ser Asn Arg Val Val
                165                 170                 175

Glu Gln Ile Lys Ser Ile Lys Val Val Thr Pro Val Glu Leu Phe Asp
            180                 185                 190

Tyr Lys Thr Glu Val Pro Ile Glu Ser Val Asp His Glu Ser Arg Asp
            195                 200                 205

Asn Ser Leu Ala Glu Val Glu Glu Asp Gly Lys Ala Val Gln Val Gly
            210                 215                 220

Thr Gln Pro Val Tyr Glu Val Asn Asp Gly Ala His Asn Pro Ser Ala
225                 230                 235                 240

Gln Val Leu Ser Gln Asn Asn Ile Ile Glu Thr Leu Asp Asp Lys Ser
                245                 250                 255

Lys Val Thr His Leu Arg Asn Ala Gly Ser Glu Lys Ile Arg Val
```

```
        260              265              270
```

<210> SEQ ID NO 4
<211> LENGTH: 773
<212> TYPE: PRT
<213> ORGANISM: Babesia microti Bm0985

<400> SEQUENCE: 4

```
Met Ile Asn Leu Ile Ile Phe Leu Pro Thr Val Leu Ser Tyr Val Ser
1               5                  10                  15

Ile Val Tyr Ala Ser Glu Ser Asp Leu Gly Gly Leu Leu Ser Val His
            20                  25                  30

Gln Val Thr Asn Ala Glu Asn Leu Tyr Glu Leu Gly Ile Lys Gln Leu
        35                  40                  45

Asp Ser Ser Ile Lys Leu Leu Glu Asp Ala Lys Phe Thr Gly Asn Arg
    50                  55                  60

Ile Leu Arg Asp Tyr Glu Gln Thr Val Gln Tyr Val Ala Ala His Ile
65                  70                  75                  80

Gly Pro Ser Gly Ser Phe Ile Lys Phe Ser Pro Val Ile Lys Arg Leu
                85                  90                  95

Ile Ser Gln Ile Asn Thr Leu Thr His Gly Leu Asn Asp Ala Leu Ser
            100                 105                 110

His Val Asp Pro Phe Leu Ser Lys Leu Met Asn Glu Lys Ser Gln Leu
            115                 120                 125

Val Ala Asn Lys Asn Val Ile Ser Gln Gly Ala Glu Glu Asn Ile Ser
        130                 135                 140

Lys Leu Ser Thr Gln Ser Ala Arg Asn Leu Leu Ile Ser Ile Lys Lys
145                 150                 155                 160

Ser Leu Gln Thr Leu Glu Leu Gly Glu Leu Asn Ser Arg Lys Leu Asn
                165                 170                 175

Thr Ile Ala Glu Lys Ile Gly Thr Asp Val Arg His Ala Ile Lys Ser
            180                 185                 190

Thr Asn Ser Thr Leu Asn Ile Leu Leu Gly Tyr Arg Val Thr Phe Thr
            195                 200                 205

Leu Val Ile Asp Ser Glu Asn Ile Leu Ser Asp Ser Glu Lys Phe Lys
        210                 215                 220

Ile Asn Ile Phe Ser His Ser Lys Leu Cys His Gly Thr Thr Asn Glu
225                 230                 235                 240

Val Val Asn Leu Gln His Lys Ala Lys Met Leu Phe Gln Lys Ser Leu
                245                 250                 255

Ser Glu Gly Leu Leu His Glu Asp Ile Asn Met Gly Lys Asn Tyr Ile
                260                 265                 270

Ile Arg Ile Asp Ser Tyr Ala His Glu Ser Asn Lys Leu Ala Ser Glu
                275                 280                 285

Met Asn Ala Lys Asn Tyr Ala Met Ala Ser Ser Val Arg Phe Ile Arg
        290                 295                 300

Lys Asp Ile Asp Lys Leu Lys Arg Ile Leu Asp Asp Tyr Lys Asn Ser
305                 310                 315                 320

Pro His Ser Ala Tyr Lys Arg Met Asp Val Ile His Val Glu Ile Asp
                325                 330                 335

Lys Ile Tyr Glu Ser Ile Gly Thr Ala Leu Lys Trp Ala Asn Ala Ala
            340                 345                 350

Val Lys Ser Asn Phe Ser Ile Leu Thr Ala Thr Arg Glu Thr Tyr Gln
        355                 360                 365
```

```
Ala Leu Glu Asn Leu Leu Lys Ile Ser Lys Lys Ser His Ser Ile Arg
    370                 375                 380

Ser Thr Tyr Thr Thr Gln Leu Asp Ala Asp Ser Asn Ser Gly Pro Phe
385                 390                 395                 400

Tyr Ala Ser Thr Thr Ala Ile Gly Asp Lys His Asp Pro Asp Asp Leu
                405                 410                 415

Tyr Gly Leu Lys His Ser Gly Tyr Asn Thr Ser Asn Asn Asp Ser Ser
            420                 425                 430

Ser Arg Tyr Ser Tyr Tyr Val Lys Lys Phe Gly Gly His Gly Ser Arg
            435                 440                 445

Ser Asn His Ser Thr Ser Glu Ser Gly Glu Asp Asp Cys Leu Asn Asp
    450                 455                 460

Lys Cys Cys Lys Asn Cys Glu Lys Ser Lys Pro Trp Tyr Lys Arg Phe
465                 470                 475                 480

Gly Leu Gly Ser Val Ile Ser Gly Ile Gln Asn Met Phe Gly Ala Ser
            485                 490                 495

Tyr Gln Gln Asp His Ser Asp Asp Asp His Tyr Pro Lys Phe Pro His
            500                 505                 510

Ser Pro Tyr Ile Ile Pro Thr Ala Pro Pro Ile Asp Leu Val Pro Asn
            515                 520                 525

Asp Ile His Thr Asn Thr Arg Ser Asn Ile Ile Lys Asn Gly Val Thr
    530                 535                 540

Glu Lys Val Ile Pro Met Ser Ser Pro Asn Ser Ala Gln Ser Asp His
545                 550                 555                 560

Glu Lys Lys Glu Pro Thr Ser Asp Asp Asn Lys Asn Asp Pro Val Asp
            565                 570                 575

Thr Asn Ser Thr Lys Ile Glu Asp Val Ala Glu Thr Lys Ser Ser Ile
            580                 585                 590

Glu Thr Glu Thr Val Ser Asn Asp Leu Glu Asn Lys Ala Ala Glu Thr
    595                 600                 605

Glu Glu Ser Ile Asp Thr Glu Pro Tyr Glu Ser Glu Ser Val Gly Thr
    610                 615                 620

Lys Ser Ser Thr Gly Ile Asp Asn Asp Thr Thr Val Asp Gln Asn Ser
625                 630                 635                 640

Gly Asn Gly His Asn Ala Ile Lys Thr Thr Asn Asn Pro His Ile Gln
            645                 650                 655

Ser Val Asn Pro Asp Phe Gln Pro Glu Asn Pro Asn Asn Pro His Val
            660                 665                 670

Asn His Tyr Gly Ser Phe Glu Ile Gln Ala Asn Ile Phe Gly Asn Gln
            675                 680                 685

Gly Asn Leu Glu Asn Ile Gln Arg Leu Gln Gln Asp Pro Lys Ile Asn
    690                 695                 700

Glu Leu Ile Ile Lys Gly Lys Glu Phe Phe Glu Leu Phe Asn Ala Val
705                 710                 715                 720

Lys Met Lys Leu Met Arg Gly Ser Ser Tyr Leu Asn Ser Lys Met Val
            725                 730                 735

Ser Ile Met Leu Ala Lys Ile Phe Gln Gly Ser Leu Ser Asn Leu Cys
            740                 745                 750

Tyr Asn Phe Asn Gln Asn Arg Tyr Tyr Tyr Asp Thr Gln Ala Tyr Asn
            755                 760                 765

Ser Ala Leu Ser Asn
    770
```

```
<210> SEQ ID NO 5
<211> LENGTH: 360
<212> TYPE: PRT
<213> ORGANISM: Babesia microti Bm1510

<400> SEQUENCE: 5

Met Phe Asn Phe Leu Glu Ile Ser Arg Val Phe Thr Thr Leu Thr Ile
1               5                   10                  15

Leu Ser Cys Ile Phe Ser Tyr Val Ser Ala Ser Ser Pro Ser Tyr Cys
                20                  25                  30

Asp Ala Pro Ser Gly Phe Thr Val Ile Asn Val Thr Ser Leu Leu Asp
                35                  40                  45

Gly Thr Pro Leu Pro Ile Gly Ile Thr Leu Glu Thr Asp Lys Ser Gly
        50                  55                  60

Tyr Asn Tyr Phe Thr Val Asp Arg Thr Leu Pro Gln Tyr Lys Lys Val
65                  70                  75                  80

Gly Phe Cys Leu Asn Gly Tyr Leu Asp Thr Phe Asp Thr Pro Lys Val
                85                  90                  95

Gln Thr Ile Leu His Lys Lys Phe Glu Asp Ser Val Tyr Val Ser Tyr
                100                 105                 110

Ile Asp Lys Phe Val Thr Asn Val Asp Gly Asn Ala Pro Ile Cys Thr
                115                 120                 125

Leu Thr His Ala Tyr Ser Leu Tyr Gly Gly Asp Ile Thr Ser Ala Leu
        130                 135                 140

Pro Pro Phe Thr Val Arg Lys Ile Ser Asp Gly Phe Leu Ser Arg Leu
145                 150                 155                 160

Asn Glu Arg Lys Gln Leu Ser Ser Ile Cys Ser Thr Ala Cys Gly Gly
                165                 170                 175

Leu Val Asp Val Val Gly Gly Asn Tyr Pro Lys Gly Ser Asp Ile Val
                180                 185                 190

Pro His Ser Glu Ser Val Asp Lys Val Lys Phe Ser Asp Val Leu Val
                195                 200                 205

Lys Ser Leu Thr Leu Lys Cys Gly Asp His Thr Phe Tyr Asn Phe Asp
        210                 215                 220

Arg Asp Gln Phe Ala Tyr Met Tyr Leu Phe Glu His Asp Gly Ala Lys
225                 230                 235                 240

Tyr Ala Ala Leu Ser Arg Leu Thr Pro Thr Met Ile Glu Val Ala Val
                245                 250                 255

Met Cys Lys Tyr Gly Asn Gly Val Glu Glu Lys Leu Leu Tyr Asp Asn
                260                 265                 270

Asp Ser Glu Phe Gln Gln Ala Val Leu Lys Leu Val Pro Ile Asn Ile
                275                 280                 285

Phe Ile Glu Asn Thr Ser Ser Met Pro His Gly Ala Ser Met Thr Lys
        290                 295                 300

Leu Asp Glu Asn Ile Asp Glu Ile Ala Ile Asn Arg Phe Val Leu Arg
305                 310                 315                 320

Tyr Pro Tyr Val Leu Leu Pro Gly Leu Ala Val Asp Ile Gly Lys Gly
                325                 330                 335

Asn Ala Asp Thr Ile Trp Ile Val Lys Pro Ser Glu Glu Asp Ser Glu
                340                 345                 350

Val Lys Tyr Phe Val Val Phe Gly
                355                 360

<210> SEQ ID NO 6
<211> LENGTH: 879
```

<212> TYPE: PRT
<213> ORGANISM: Babesia microti Bm0320

<400> SEQUENCE: 6

```
Met Lys Leu Phe Tyr Val Trp Val Ser Leu Ala Phe Leu Gly Ser Thr
1               5                   10                  15

Ile Val Thr Gly Arg Pro Ala Asn Ser Asn Asp Tyr Leu Thr Thr Ser
            20                  25                  30

Ser Ser Asp Ser Asp Ser Ser Glu Ser Glu Ser Glu Leu Asp Gly Leu
        35                  40                  45

Ser Asp Leu Glu Asp Ala Ser Asp Ala Glu Phe Asp Asp Ile Tyr Asn
    50                  55                  60

Val Glu Asp Leu Thr Ser Asn Val Asp Gly Asn Leu Ala Lys Phe Gly
65                  70                  75                  80

His Phe Asp Gly Lys Asp Thr Lys Asn Glu Asp Thr Ser Ala Ser Leu
                85                  90                  95

Asp Leu Asn Lys Trp Asn Asn Ser Ser Arg Lys Lys Ser Gly Asn Lys
            100                 105                 110

Val Lys Phe Ser Ser Asn Lys Ser Lys Ser Thr Thr Lys Lys Lys Arg
        115                 120                 125

Lys Lys Thr Tyr Ser Thr Asn Glu Asn Gly Asn Lys Leu Lys Phe Glu
    130                 135                 140

Asp Lys Lys His Val Glu His Lys Lys Leu Ser Ser Lys Lys Lys Leu
145                 150                 155                 160

Lys Gln Gln Gln Leu Asn Glu Gln His Gly Ile Lys Pro Ile Asn Ala
                165                 170                 175

Ser Asn Asp Thr Asp Met Lys His Gly Leu Lys Ser Gly Lys Ser Ser
            180                 185                 190

Ser Lys His Gly Ile Lys Ala His Thr Phe Asp Ser Gln Thr His Ile
        195                 200                 205

Ile Thr Asn Gln Ile Gly Thr Asp Gln Ile Gln Leu Arg Asp Ser Glu
    210                 215                 220

Ile Glu Asn Lys Val Tyr Lys Lys Leu Val Ala Glu Leu Asn Lys Thr
225                 230                 235                 240

Pro Asp Leu Asp Ile Ala Gly Ile Ser Glu Ser Ile Arg Tyr Leu Gly
                245                 250                 255

Ser Gly Tyr Asp Ile Ile Phe Gly Asn Pro Ile Gly Asp Pro Leu Met
            260                 265                 270

Met Val Asp Pro Gly Tyr Arg Asn Pro Ile Ile Gln Leu Glu Trp Asp
        275                 280                 285

Lys His Ser Thr Phe Ala His Asn Asn Ser Leu Pro Gln Pro Val Asp
    290                 295                 300

Gly Trp Val Arg Pro Glu Ile Ser Cys Lys Gln Ala Glu Lys Val Asp
305                 310                 315                 320

His Val Asn Thr Leu Glu Asp Tyr Lys Lys Glu Leu Ser Val Asp Ala
                325                 330                 335

Val Ala Ser Ser Asp Phe Leu Asn Phe Phe Ala Phe Ser Ala Ser Gly
            340                 345                 350

Gly Tyr Lys Asn Phe Ala Lys Leu Val Thr Gln Glu Lys Thr Arg Ser
        355                 360                 365

Phe Ile Leu Lys Thr Tyr Cys Leu Arg Tyr Ile Ala Gly Leu Glu Val
    370                 375                 380

Ser Thr Asn Leu Lys Leu Thr Pro Ala Phe Lys Asn Ala Val Asp Lys
385                 390                 395                 400
```

-continued

```
Leu Pro Val Ile Phe Asp Gly Phe Glu Glu Tyr Ser Ser Cys Pro Ile
            405             410             415

Glu Lys Tyr Lys Ala Asn Glu Ser Asp Thr Asp Cys Glu Ser Asn Val
            420             425             430

Arg Pro Trp Met Asp Phe Phe Lys Glu Phe Gly Thr His Phe Thr Ser
            435             440             445

Val Val His Leu Gly Gly Lys Met Thr Tyr Gln Val Gln Met Lys Gln
            450             455             460

Ser Asp Ile Asn Lys Leu Gln Glu Gln Gly Val Asn Val Asp Ala Ala
465             470             475             480

Ile Lys Ala Thr Cys Gly Phe Gly Met Pro Asn Ile Ser Gly Lys Ile
                485             490             495

Ser Thr Lys Gly Glu Ser Thr Ser Ile Ser Lys Met Ser Asp Tyr Lys
            500             505             510

Val Glu Lys Met Ile Met Val Ile Gly Gly Glu Pro Pro Lys Asp Leu
            515             520             525

Asn Asp Ser Ser Asn Leu Asn Asn Trp Ala Lys Ser Val Ala Lys Ser
    530             535             540

Pro Met Pro Ile Lys Ser Glu Leu Ile Pro Ile Arg Glu Leu Phe Asp
545             550             555             560

Leu His Glu Leu Gln Gln Ser Tyr Asn Gln Ala Ile Lys Tyr Tyr Ser
            565             570             575

Glu Val Tyr Gly Ile Ser Gln Asn Asp Met Tyr Glu Ile Lys Gly Lys
            580             585             590

Ile Lys Gly Ile Pro Glu Ile Ile Lys Glu Ala Gln Gln Val Thr Tyr
            595             600             605

Asp Gly Pro Ala Pro Gly Arg Val Val Cys Pro Ile Gly Thr Thr Ile
    610             615             620

Leu Phe Gly Phe Ser Met Thr Ile Thr Lys Lys Lys Ala Leu Asp
625             630             635             640

Phe Leu Lys Asn Thr Ser Tyr Asn Val Asn Ile Val Pro Cys Val Val
            645             650             655

Gly Asn Glu Lys Cys Ser Gly Thr Ala Gln Ser Asp Ser Ile Val Lys
            660             665             670

Ile Trp Ala Leu Cys Ser Pro His Pro Ala Pro Leu Leu Val Gln Val
            675             680             685

Ser Ser His Lys Asn Asn Gly Pro Ala Thr Val Glu Cys Pro Lys Gly
            690             695             700

Phe Val Ile Gly Met Gly Phe Gly Ile Thr Phe Pro Lys Gly Leu Pro
705             710             715             720

Ile Met Pro Gln Asp Ile Tyr Pro Cys Arg Asn Gly Gln Thr Ser Cys
                725             730             735

Thr Lys Ile Pro Asp Lys Asp Gly Ser Thr Thr Val Trp Ala Val Cys
            740             745             750

Phe Glu Ser Gly Ala Ile Glu Val Asp Asn Leu Thr Asn Asn Ala Lys
            755             760             765

Ala Gly Ser Ser Ala Ser Cys Glu Ala His Asp His Ile Thr Ser Gly
    770             775             780

Leu Val Asn Thr Cys Pro Asp Asp Tyr Glu Val Leu Cys Gly Phe Ser
785             790             795             800

Met Ala Leu Thr Arg Lys Asn Ser His Thr Asp Asp His Phe Lys Ala
            805             810             815
```

-continued

```
Cys Arg Gly Gly Lys Ser Cys Ala Ile Asp Lys His Lys Arg His Asp
            820                 825                 830

Asn Glu Cys Ile Ala Tyr Ala Ser Trp Asn Val Cys Ser Leu Val Val
            835                 840                 845

Pro Gly His Lys Asp Thr Val His Pro Ala Arg Ala Asn Val Thr Leu
            850                 855                 860

Asp Arg Thr Lys Thr Ala Asn Gly Ile Glu Pro Ile Gly Lys Asn
865                 870                 875

<210> SEQ ID NO 7
<211> LENGTH: 322
<212> TYPE: PRT
<213> ORGANISM: Babesia microti Bm9435

<400> SEQUENCE: 7

Met Ser Leu Trp Tyr Ala Val Ile Leu Ala Leu Gly Tyr Ile Asn Ser
1               5                   10                  15

Glu Cys Lys Asn Val Asn Arg Ser Ile Arg Ser Lys Val Tyr Asn Asn
            20                  25                  30

His Ser Asn Asp Met Pro Ile Asn Pro Val Lys Val Gln His Gln Lys
        35                  40                  45

His Asn Pro Trp Arg Thr Lys Phe Met Lys Phe Asp Ser Asp Asn Glu
    50                  55                  60

Glu Glu Gly Asn Glu Asn Asp His Asp Glu Asp Asn Val Glu Glu Gly
65                  70                  75                  80

Glu Glu Val Leu Asp Ser Glu Lys Ser Lys Thr Ser Ser His Ile Val
                85                  90                  95

Asn Pro Thr Gly Thr Ser Lys Asp Asp Asn Thr Ile Glu Asn Asp Asn
            100                 105                 110

Glu Tyr Lys Pro Arg Val Cys Gly Gln Gly Lys Arg Gly Ile Leu Ile
            115                 120                 125

Tyr Gln Gln Gln Asp Tyr Gly Ile Ala Ile Met Gly Leu Ile Asp Lys
    130                 135                 140

Gly Thr Leu Lys Leu Tyr Ala Gly Asn Ile Ile Leu Lys Glu Ile Ser
145                 150                 155                 160

Leu Trp Asn Ile Ile Ser Pro Ile Glu Met Ala Asn Asn Lys Cys Phe
                165                 170                 175

Ser Ile Arg Gln Pro Thr Gln Leu Pro Thr Ile Leu Cys Ala Gly Gly
            180                 185                 190

Ile Asp Ser Arg Asn Arg Trp Val Asn Ala Leu Glu Ser Ser Arg Leu
            195                 200                 205

Cys Leu Ile Thr Lys Val Lys Tyr Tyr Leu Pro Ile Ser Ile Asp Lys
    210                 215                 220

Asp Phe Val Glu Pro Glu Asp Pro Pro Ser Gly Ile Asn Val Phe
225                 230                 235                 240

Ile Ala Glu Ser Gln Phe Gly Lys Pro Glu Ile Val Ile Asn Gly Lys
                245                 250                 255

Thr Leu Glu Gln Ile Lys Asn Asp Glu Met Glu Ser Ile Ser Thr Ser
            260                 265                 270

Asp Glu Tyr Gly Thr Thr Leu Trp Asn Gly Glu Leu Gln Lys Pro Asp
            275                 280                 285

Phe Gln Glu Asp Glu Phe Asn Gly Asp Glu Ser Met Glu Ser Leu Ala
    290                 295                 300

Glu Ala Glu Met Lys Lys Asp Ile Ala Pro Glu Phe Gly His Ala Arg
305                 310                 315                 320
```

-continued

Met Phe

<210> SEQ ID NO 8
<211> LENGTH: 405
<212> TYPE: PRT
<213> ORGANISM: Babesia microti Bm2975

<400> SEQUENCE: 8

Met Lys Gly Ile Gly Pro Leu Ser Thr Ile Tyr Val Leu Ser Ala Ile
1               5                   10                  15

Ile Gly Val Ser Ile Gly Val Arg Val Gly Val Met Gln His Asn Lys
                20                  25                  30

Lys Pro Lys Val Val Asn Ala Val His Asn Val Tyr Ala Ser Leu Ile
            35                  40                  45

Asp Thr Asn Ser Ser Asn Ser Val Thr Pro Thr Ala Ser Thr Gln Lys
        50                  55                  60

Asn Thr Thr Glu Asn Thr Asn Thr Thr Thr Pro Asp Pro Asn Val Asn
65                  70                  75                  80

Ser Thr Asp Thr Lys Glu Lys Asp Asn Asn Ala Thr Glu Ile Asp Asp
                85                  90                  95

Lys Ser Ile Asn Pro Lys Cys Ile Gly Glu Ile Ile Lys Pro Phe Ser
            100                 105                 110

Ile Glu Ser Lys Thr Phe Thr Ile His Gly Gly Gly Ala Gly Val Glu
            115                 120                 125

Asn Ser Gly Lys Trp Ile Ser Asn Ala Ser Asp Ile Asp Thr Asn Leu
        130                 135                 140

Glu Thr Phe Leu Thr Ile Lys Phe Glu Met Asn Ser Gln Ile Tyr Ser
145                 150                 155                 160

Tyr Ile Asn Asp Leu Gly Gln Asn Met Thr Ala Thr Ile Asn Leu Lys
                165                 170                 175

Met Ser Pro Asp Leu Lys Asp Phe Gly Tyr Ser Cys Pro Lys Asn Thr
            180                 185                 190

Val Ser Val Val Asp Gly Glu Phe Ser Asn Val Glu Thr Leu Leu Thr
            195                 200                 205

Glu Lys Leu Lys Phe Phe Ser Gly Val Phe Asn Lys Glu Thr Asn Arg
        210                 215                 220

Val Asp Ile Asp Ile Thr Lys Leu Ile Arg Asp Lys Phe Leu Gly Val
225                 230                 235                 240

Gly Asp Ser Gly Glu Asn Val Leu Asn Leu Ala Val Lys Ser Gly Asn
                245                 250                 255

Lys Cys Ile Tyr Arg Ile His Phe Lys Glu Asn Pro Pro Thr Ile Lys
            260                 265                 270

Ile Ile Pro Lys Asn Thr Thr Tyr Ile Gln Thr Asp Lys Trp Thr Ala
            275                 280                 285

Cys Ser Lys Glu Cys Lys Lys Glu Gly Ala Tyr Gln Cys Ala Pro Ile
        290                 295                 300

Lys Cys Ile Glu Gly Asn Glu Lys Cys Asp Thr Thr Lys Met Phe Ser
305                 310                 315                 320

Lys Arg Glu Cys Val Asp Val Glu Asp Cys Val Asn Val Glu Glu His
                325                 330                 335

Ile Asn Thr Lys Asn Ser Ile Gly Gly Trp Asp Leu Asn Leu Ser Asn
            340                 345                 350

Ile Phe Leu Lys Ser Pro Leu Tyr Ile Gly Leu Cys Val Ala Leu Val
            355                 360                 365

```
Ile Leu Leu Ala Ile Ala Gly Ile Val Val Phe Gln Lys Met Lys Gly
    370             375             380

Gln Lys Tyr Val Gln Ile Thr Asp Glu Glu Ile Val Gly Ser Val Phe
385                 390             395             400

Thr Gly Gly Cys Ile
                405

<210> SEQ ID NO 9
<211> LENGTH: 535
<212> TYPE: PRT
<213> ORGANISM: Babesia microti Bm3280

<400> SEQUENCE: 9

Met Val Asn Leu Ser Ile Pro Gly Leu Leu Leu Leu Ser Ala Tyr Ser
1               5               10              15

Leu Asn Ser Ala Ser Ala Gly Asp Val Tyr Glu Ile Ser Ser Gly Asn
                20              25              30

Pro Pro Asp Ile Glu Pro Thr Ser Thr Ser Leu Glu Thr Asn Val Val
            35              40              45

Thr Asn Tyr Ile Pro Glu Pro Asn Ala Asp Ser Glu Ser Val His Val
        50              55              60

Glu Ile Gln Glu His Asp Asn Ile Asn Pro Gln Asp Ala Cys Asp Ser
65              70              75              80

Glu Pro Leu Glu Gln Met Asp Ser Asp Thr Arg Val Leu Pro Glu Ser
                85              90              95

Leu Asp Glu Gly Val Pro His Gln Phe Ser Arg Leu Gly His His Ser
            100             105             110

Asp Met Ala Ser Asp Ile Asn Asp Glu Glu Pro Ser Phe Lys Ile Gly
        115             120             125

Glu Asn Asp Ile Ile Gln Pro Pro Trp Glu Asp Thr Ala Pro Tyr His
    130             135             140

Ser Ile Asp Asp Glu Glu Leu Asp Asn Leu Met Arg Leu Thr Ala Gln
145             150             155             160

Glu Thr Ser Asp Asp His Glu Glu Gly Asn Gly Lys Leu Asn Thr Asn
                165             170             175

Lys Ser Glu Lys Thr Glu Arg Lys Ser His Asp Thr Gln Thr Pro Gln
            180             185             190

Glu Ile Tyr Glu Glu Leu Asp Asn Leu Leu Arg Leu Thr Ala Gln Glu
        195             200             205

Ile Tyr Glu Glu Arg Lys Glu Gly His Gly Lys Pro Asn Thr Asn Lys
    210             215             220

Ser Glu Lys Ala Glu Arg Lys Ser His Asp Thr Gln Thr Thr Gln Glu
225             230             235             240

Ile Cys Glu Glu Cys Glu Glu Gly His Asp Lys Ile Asn Lys Asn Lys
            245             250             255

Ser Gly Asn Ala Gly Ile Lys Ser Tyr Asp Thr Gln Thr Pro Gln Glu
            260             265             270

Thr Ser Asp Ala His Glu Glu Gly His Asp Glu Ile Asn Thr Asn Lys
            275             280             285

Ser Glu Lys Ala Glu Arg Lys Ser His Asp Thr Gln Thr Thr Gln Glu
        290             295             300

Ile Cys Glu Glu Cys Glu Glu Gly His Asp Lys Ile Asn Lys Asn Lys
305             310             315             320

Ser Gly Asn Ala Gly Ile Lys Ser Tyr Asp Thr Gln Thr Pro Gln Glu
```

-continued

```
                325                 330                 335

Thr Ser Asp Ala His Glu Glu Glu His Gly Asn Leu Asn Lys Asn Lys
            340                 345                 350

Ser Gly Lys Ala Gly Ile Lys Ser His Asn Thr Gln Thr Pro Leu Lys
            355                 360                 365

Lys Lys Asp Phe Cys Lys Glu Gly Cys His Gly Cys Asn Asn Lys Pro
        370                 375                 380

Glu Asp Asn Glu Arg Asp Pro Ser Ser Pro Asp Asp Asp Gly Gly Cys
    385                 390                 395                 400

Glu Cys Gly Met Thr Asn His Phe Val Phe Asp Tyr Lys Thr Thr Leu
                405                 410                 415

Leu Leu Lys Ser Leu Lys Thr Glu Thr Ser Thr His Tyr Tyr Ile Ala
                420                 425                 430

Met Ala Ala Ile Phe Thr Ile Ser Leu Phe Pro Cys Met Phe Lys Ala
                435                 440                 445

Phe Arg Ala Ile Ile Ser His Lys Leu Arg Lys Asn Gly Ser Asn Ala
        450                 455                 460

Lys Leu Ala Leu Ser Met Phe Leu Ser Phe Ile Phe Ser Leu Ile Ile
    465                 470                 475                 480

Leu Thr Leu Asp Tyr Gly Leu Met Leu Leu Ala Met Thr Phe Asn Val
                485                 490                 495

Gly Tyr Phe Phe Ala Ile Ile Ile Gly Ser Ser Leu Ser Tyr Thr Met
                500                 505                 510

Phe Gly Leu Leu Phe Asp Ser Pro Cys Asp Cys Gly Gly Lys Lys Ala
            515                 520                 525

Ile Leu Ser Asp Cys Cys Gly
    530                 535

<210> SEQ ID NO 10
<211> LENGTH: 456
<212> TYPE: PRT
<213> ORGANISM: Babesia microti Bm3430

<400> SEQUENCE: 10

Met Gly Tyr Leu Ser Leu Asn Ile Ile Val Thr Ser Leu Val Thr Leu
1               5                   10                  15

Val Ala Asn Val Ser Ala Val Leu Pro Asp Ile Leu Ser Gln Asn Asn
            20                  25                  30

Thr Phe Lys Ser Phe Leu Glu Val Asn Asn Val Asp Gln Glu Asp Leu
        35                  40                  45

Ile Cys Asn Lys Ala Leu Cys Lys Ser Thr Asp Ser Ile Asn Arg Asn
    50                  55                  60

Thr Ser Ser Tyr Cys Tyr Lys Tyr Lys Leu Cys Ser Lys Cys Ser Val
65                  70                  75                  80

Ser Asn Val Pro Asp His Pro Val Cys Tyr Leu Leu Asp Asn Asp His
                85                  90                  95

Asn Tyr Ile His Leu Met Glu Gly His Leu Gly Ser Gln Pro Ile Gly
            100                 105                 110

Ser Ala Asn Ser His Asp Asn Ser Ser His Asp Glu His Ser Ser His
            115                 120                 125

Ser Asn Asn Gly Asp Met Met Asp Glu His Glu Glu Glu Asn Phe Leu
        130                 135                 140

Gln Glu Tyr Glu Ser Lys Ser Met Lys Phe Ile Pro Thr Ser Asn Met
145                 150                 155                 160
```

-continued

```
Ser Asp Phe Asp His Ala Arg Arg Ser Cys Ala Val Asp Ser Lys Gly
            165                 170                 175

Asn Val Met Ile Ser Val Arg Leu Ile Ile Gln Trp Tyr Met Ser Lys
            180                 185                 190

Asp Lys Ser Asn Asn Gln Gln His His Gly Asn Asp Asp Asp Ser Gln
            195                 200                 205

Asn Tyr Asp Ala Asn Tyr Leu Gln Leu Thr Pro Met Tyr Ser Asp Asp
        210                 215                 220

Ser Val Asn Ser Ser Met Leu Glu Met Asp His Asp Asp Ser Glu Ser
225                 230                 235                 240

Ser Asn Ser His Lys Ser Arg Met Ala Asn Met Ala Lys Asn Phe Gln
            245                 250                 255

Val Leu Lys Asn Ile His Lys Ser Ala Val Lys Arg Tyr Lys Ser Pro
            260                 265                 270

Lys Ala Lys Ile Tyr Leu Ile Phe Ser Asn Pro Lys Ile Asn Ser Cys
            275                 280                 285

Arg His Pro Val Ile Tyr Asn Gly Lys Ile Ser Pro Ser Ser Met Phe
        290                 295                 300

Val Ala Lys Leu Glu Ser Thr Ile Ser Gln Ile Asp Leu Thr Gln Asp
305                 310                 315                 320

Leu Ile Lys Ser Ser Ile Glu Thr Ile Val Ser Cys Glu Ala Cys Asp
            325                 330                 335

Lys Leu Lys Tyr Asn Ser Cys Ile Gln Val Thr Cys Ala Lys Asn Thr
            340                 345                 350

Pro Gly Ala Ala Ser Leu Ala Met Gly Ser Ala Val Tyr Val Pro Met
            355                 360                 365

Thr Asn Thr Thr Ile Gly Val Asn Ala His Asn Pro Asn Ala Val Val
        370                 375                 380

Ala Ala Gly Ile Pro Met Gly Lys Ile Pro Val Ile Pro His Pro Ala
385                 390                 395                 400

Ala Ile Ser Gly Gly Asn Val Gly His Leu Asn Asn Gly Leu His Lys
            405                 410                 415

Ala Val Asn Asn Ala Val Met Met Pro Asn Gly Thr Ser Leu Pro Val
            420                 425                 430

Gln Ser Gly Val Val Ile Lys Ser Leu Tyr Asn Cys Leu Ala Phe Leu
            435                 440                 445

Leu Thr Ile Leu Tyr Leu Asn Phe
        450                 455

<210> SEQ ID NO 11
<211> LENGTH: 349
<212> TYPE: PRT
<213> ORGANISM: Babesia microti Bm0690

<400> SEQUENCE: 11

Met Glu Val Glu Arg Ile Leu Phe Lys Ser Thr Ile Phe Leu Met Phe
1               5                   10                  15

Ile Arg Tyr Thr Asn Ala Ile Leu Phe Asp Thr Tyr Leu Gln Val Val
            20                  25                  30

Ser Glu Asn Asp Cys Asn Pro Lys Cys Leu Gln Gly His Thr Cys Ile
            35                  40                  45

Leu Asn Arg Lys Thr Asn Lys Lys Ser Cys Thr Cys Pro Pro Asn His
        50                  55                  60

Tyr Tyr Asp Glu Asn Phe Gly Cys Gln Met Val Ile Thr Cys Pro Leu
65                  70                  75                  80
```

-continued

```
Cys Arg His Ala Asn Pro Trp Gly Thr Thr His Thr Val Pro Asn Thr
                85                  90                  95

Ala Leu Pro Gly Gln His Lys Ser Gly Tyr Gln Tyr Ser Ile Cys Lys
            100                 105                 110

Asp Gly His Thr Lys Asp Glu Met Arg Thr Phe Cys Arg Arg Tyr Asn
            115                 120                 125

Ala Cys Glu Arg Gly Ala Lys Ile Cys Pro Glu His Ser Thr Cys Ile
        130                 135                 140

Ile Asp Asn Lys Gly His Ala Val Cys Asn Leu Asp Asn Gly Tyr Arg
145                 150                 155                 160

Trp His Asp Asn Thr Lys Lys Gly Ala Val Arg Ile Glu Tyr Cys Gly
                165                 170                 175

Gly His Asn Lys Asn Lys Cys Ile Pro Pro Ala Thr Cys Gln Glu Val
            180                 185                 190

Asn Asn Ala Asn Ser Asn Thr Leu Thr Val Cys Ser Cys Pro Ser Glu
            195                 200                 205

Met Tyr Leu Thr Arg Asn Lys Arg Gln Cys Ser Lys Gln Gln Gln Phe
        210                 215                 220

Ser Asp Asn Lys Val Tyr Ser Ile Ser Val Lys Asn Arg Thr Glu Lys
225                 230                 235                 240

Phe Pro Glu Asn Phe Lys Val Phe Leu Asp Gly Cys Phe Asp Val Gln
                245                 250                 255

Leu Asp Gly Lys Glu Gly Val Val Ile Tyr Lys Ser Ser Asp Thr Val
            260                 265                 270

Ser Ser Ile Lys Ser Ile Val Asn Ile Pro Thr Asp Leu Lys Ser Ile
        275                 280                 285

His Phe Glu Met Lys Phe Lys Thr Leu Asn Ile Phe Val Glu Asn Gly
        290                 295                 300

Asn Asp Met His Pro Ile Phe Ser Ile Lys Phe Asp His Ser Asp Cys
305                 310                 315                 320

Lys Phe Ile Glu Ser Ile Glu Gly Leu Glu Ile Gly Asp Asp Ile Leu
            325                 330                 335

Arg Thr Glu Ser Asn Met Arg Asp Leu His Pro Thr Leu
            340                 345
```

<210> SEQ ID NO 12
<211> LENGTH: 328
<212> TYPE: PRT
<213> ORGANISM: Babesia microti BMGP112

<400> SEQUENCE: 12

```
Met Val Ser Phe Lys Pro Thr Ile Ile Thr Ala Phe Ala Ala Phe Leu
1               5                   10                  15

Ala Phe Gly Asn Ile Ser Pro Val Leu Ser Ala Gly Gly Ser Gly Gly
            20                  25                  30

Asn Gly Gly Asn Gly Gly Gly His Gln Glu Gln Asn Asn Ala Asn Asp
        35                  40                  45

Ser Ser Asn Pro Thr Gly Ala Gly Gly Gln Pro Asn Asn Glu Ser Lys
        50                  55                  60

Lys Lys Ala Val Lys Leu Asp Leu Asp Leu Met Lys Glu Thr Lys Asn
65                  70                  75                  80

Val Cys Thr Thr Val Asn Thr Lys Leu Val Gly Lys Ala Lys Ser Lys
                85                  90                  95

Leu Asn Lys Leu Glu Gly Glu Ser His Lys Glu Tyr Val Ala Glu Lys
```

```
                100              105              110

Thr Lys Glu Ile Asp Glu Lys Asn Lys Lys Phe Asn Glu Asn Leu Val
        115              120              125

Lys Ile Glu Lys Arg Lys Lys Ile Lys Val Pro Ala Asp Thr Gly Ala
    130              135              140

Glu Val Asp Ala Val Asp Asp Gly Val Ala Gly Ala Leu Ser Asp Leu
145              150              155              160

Ser Ser Asp Ile Ser Ala Ile Lys Thr Leu Thr Asp Asp Val Ser Glu
                165              170              175

Lys Val Ser Glu Asn Leu Lys Asp Asp Glu Ala Ser Ala Thr Glu His
            180              185              190

Thr Asp Ile Lys Glu Lys Ala Thr Leu Leu Gln Glu Ser Cys Asn Gly
            195              200              205

Ile Gly Thr Ile Leu Asp Lys Leu Ala Glu Tyr Leu Asn Asn Asp Thr
    210              215              220

Thr Gln Asn Ile Lys Lys Glu Phe Asp Glu Arg Lys Lys Asn Leu Thr
225              230              235              240

Ser Leu Lys Thr Lys Val Glu Asn Lys Asp Glu Asp Tyr Val Thr His
            245              250              255

Phe Arg Asp Met Ala Thr Glu Ala Gln Asn Ala Val Gly Glu Val Lys
            260              265              270

Lys Ala Ile Asp Ala Val Val Ala His Arg Lys Ala Glu Asn Leu Asp
            275              280              285

Val Asp Asp Thr Leu Phe Ser Asn Leu Ser Thr Leu Leu Asp Thr Ile
    290              295              300

Ile Glu Thr Ser Arg Ala Tyr Leu Pro Gly Val Ala Phe Ala Leu Leu
305              310              315              320

Ser Ser Val Ala Met Phe Leu Phe
            325
```

<210> SEQ ID NO 13
<211> LENGTH: 438
<212> TYPE: PRT
<213> ORGANISM: Babesia microti BMIPA48

<400> SEQUENCE: 13

```
Met Arg Gly Met Phe Ser Asn Lys Trp Met Ser Phe Val Cys Phe Ser
1               5               10              15

Ile Leu Phe Val Ala Leu Lys Ser Asp Leu Glu Tyr Val Ser Ala Leu
            20              25              30

Lys Leu Leu Arg Ala Pro Pro Gln Thr Ser Leu Phe Leu Glu Lys Leu
        35              40              45

Ile Asp Asp Gly Ser Asp Ile Pro Lys Asp Pro Ile Asp Thr Asp Lys
    50              55              60

Glu Glu Ser Gln Ser Ser Leu Phe Lys Phe Asn Leu Asn Leu Phe Asn
65              70              75              80

Lys Lys Ser Ile Trp Glu Ala Asp Glu Lys Phe Val Ile Thr Leu Ala
                85              90              95

Lys Ser Arg Leu Asn Val Ile Leu Ala Gln Lys Leu Asp Lys Phe Leu
            100              105              110

Ala Lys Thr Cys Lys Ile Tyr Thr Val Asp Ser Glu His Ser Ala Cys
            115              120              125

Ile Asn Asp Ile Lys Ile Tyr Ala Gln Lys Cys Ile Glu Ser Asn Asp
    130              135              140
```

-continued

```
Leu Asn Ser Cys Tyr Val Ile Pro Ile Gln Pro Ile Ala Lys Leu Pro
145             150                 155                 160

Thr Ser Arg Leu Tyr Gly Leu Val Pro His Val Leu Asn Phe Ser Ile
                165                 170                 175

Leu Ile Phe Thr Asn Leu Arg Ser Asn Leu Asp Arg Tyr Tyr Ile Asp
            180                 185                 190

Gly Ser Lys Asp Trp Phe Ser His Ile Phe Met Arg Leu Lys Arg Phe
            195                 200                 205

Phe Gly Ile Arg Asn Lys His Ser Tyr Phe Ser Asp Asn Arg Leu Met
    210                 215                 220

Asn Lys Ile Phe Ser Arg Thr Ser Thr Thr Phe Gly Pro Asp Arg Ser
225                 230                 235                 240

Asp Ser Leu Leu Ser Asn Tyr Ile Lys Phe Gly Ala Ile Glu Tyr Ala
                245                 250                 255

Ile Leu Leu Asn Thr Arg Ser Asn Leu Val Lys Met Ile Leu Ser Ser
                260                 265                 270

Phe Ala His Ile Lys Phe Val Arg Lys Arg Leu Tyr Lys Phe Tyr Thr
            275                 280                 285

Asn Lys Trp Lys Ser Ile Glu Gly Leu Val Thr Arg Gly His Leu Lys
    290                 295                 300

Pro Val Asp Leu Ser Asn Asn Pro Ile Ser Asp Asn Ile Phe Lys Tyr
305                 310                 315                 320

Phe Gly Lys Phe Ser Asn Asn Thr Asn Leu Ser Asn Ala Ile Ala Gly
                325                 330                 335

Ala Phe Leu Asp His Tyr Lys Ser Leu Phe Ser Asn Ser Thr Asp Val
            340                 345                 350

Asn Gly Glu Gly Ser Ser Gly Glu Gly Pro Ser Gly Glu Gly Phe Asn
            355                 360                 365

Gly Glu Gly Ser Ser Gly Glu Gly Pro Ser Gly Glu Gly Phe Asn Gly
        370                 375                 380

Glu Gly Phe Asp Gly Glu Gly Pro Ser Gly Glu Gly Pro Ser Gly Glu
385                 390                 395                 400

Gly Phe Asn Gly Glu Gly Phe Asn Gly Glu Gly Leu Asn Gly Glu Gly
                405                 410                 415

Pro Ser Gly Glu Gly Pro Ser Gly Glu Gly Leu Asn Glu Trp Asn Gly
            420                 425                 430

Leu Met Asn Gly Thr Ala
            435
```

```
<210> SEQ ID NO 14
<211> LENGTH: 132
<212> TYPE: PRT
<213> ORGANISM: Babesia duncani BdGPI6

<400> SEQUENCE: 14

Met Ala Arg Phe Phe Ser Tyr Lys Lys Leu Ile Ala Phe Ala Ile Val
1               5                   10                  15

Ala Leu Ala Ser Leu Lys Glu Val Ser Phe Leu Gly Gly Cys Pro Tyr
                20                  25                  30

Ala Leu Ala Val Ala Thr Thr Thr Thr Thr Gly Thr Asn Gly Ala Ala
            35                  40                  45

Thr Gly Thr Asn Gly Ala Ala Thr Gly Thr Asn Gly Ala Gly Ala Asn
        50                  55                  60

Asp Thr Ser Lys Asn Thr Ser Asp Pro Asn Thr Pro Ala Thr Pro Pro
65                  70                  75                  80
```

```
Ser Ser Pro Glu Ser Asn Lys Asp Asn Ala Ala Gly Gly Ser Asp Gly
                85                  90                  95

Gln Lys Pro Thr Gly Gln Asp Pro Gln Lys Pro Asn Ala Gly Asn Gly
            100                 105                 110

Phe Ala Ala Thr Ser Val Ile Gly Ala Ala Thr Ile Gly Leu Leu Thr
            115                 120                 125

Leu Ala Phe Asn
    130

<210> SEQ ID NO 15
<211> LENGTH: 242
<212> TYPE: PRT
<213> ORGANISM: Babesia duncani BdGPI8

<400> SEQUENCE: 15

Met Asn Leu Lys Trp Leu Leu Gly Leu Ala Leu Ile Gly Ser Lys Tyr
1               5                   10                  15

Ala Leu Gly Gly Asp Pro Asn Asp Ser Glu Val Asp Ser Gly Lys Glu
            20                  25                  30

Arg Gly Pro Gly Lys Arg Met Thr Phe Asp Glu Leu Leu Asp Glu Leu
            35                  40                  45

Lys Thr Ala Glu Ala Ser Val Leu Gly Ile Lys Ala Glu Ile Asn Gly
    50                  55                  60

Gly Leu Asn Arg Leu Arg Tyr Arg Ile Gly Asn Leu Asp Ala Ile Thr
65                  70                  75                  80

Lys Ser Asp Tyr Asp Glu Ile Ser Asp Ala Ile Arg Asp Ile Ile Thr
                85                  90                  95

Lys Arg Thr Glu Phe Ala Lys Ala Val Asn Lys Arg Val Gln Leu Glu
            100                 105                 110

Ala Ile Ala Asn Lys Phe Ser Glu Arg Thr Ser Met Gly Asn Leu Glu
            115                 120                 125

Asp Ile Gln Phe Ser Thr Phe Trp Val Lys Leu Glu Ala Ile Thr Arg
    130                 135                 140

Val Pro Asp Phe Gln Leu Lys Glu Asp Phe Val Lys Met Lys Asp Glu
145                 150                 155                 160

Ile Ile Asp Val Lys Glu Lys Phe Ile Glu Lys Leu Lys Lys Ala Arg
                165                 170                 175

Glu Ala Thr Ala Glu Val Ile Pro Glu Thr Ile Val Glu Asp Gln Glu
            180                 185                 190

Met Lys Ser Asp Leu His Glu Glu Ile Lys Ser His Gly Asp Asp Asp
            195                 200                 205

Ile Phe Asn Asp Lys Ser Asp Lys Lys Gln Asn Ser Gly Phe Ala Ala
    210                 215                 220

Thr Ser Ser Ser Leu Ile Leu Leu Ala Met Ala Thr Ile Gly Tyr Ser
225                 230                 235                 240

Leu Phe

<210> SEQ ID NO 16
<211> LENGTH: 618
<212> TYPE: PRT
<213> ORGANISM: Babesia duncani BdGPI17

<400> SEQUENCE: 16

Met Asp Val Phe Ser Ile Leu Leu Val Phe Ser Ala Phe Tyr Val Asn
1               5                   10                  15
```

-continued

Ala Ile Ala Ala Asp Asp Val Lys Thr Phe Leu Phe Lys Lys Asp Val
            20                  25                  30

Glu Ser Thr Val Glu Ile Asp Ala Asn Asp Asp Ala Val Leu Val Cys
            35                  40                  45

Pro Ile Ala Ser Val Leu Ile Ile Lys Lys Ala Arg Trp Leu Pro Val
            50                  55                  60

Thr Gly Gly Asp Met Arg Val Lys Asp Gly Phe Ser Arg Thr Thr Arg
65                  70                  75                  80

Ile Gly Trp Leu Cys Asn Gly Leu Glu Asn Cys Ala Phe Arg Pro Val
                    85                  90                  95

Ala His Leu Ser Lys Ile Gly Asp Arg Tyr Glu Phe Leu Gly Gln Pro
            100                 105                 110

Ile Glu Thr Asp Ile Tyr Lys Leu Thr Val Thr Ala Thr Cys Gly Asn
            115                 120                 125

Phe Met Phe Lys Arg Pro Gly Arg Arg Glu Met Leu Cys Ile Pro Thr
            130                 135                 140

Ser Ala Lys Pro Asp Ile Val Leu Gly Cys Lys Asp Asn Glu Ala Ile
145                 150                 155                 160

Glu Leu Ser Tyr Val Arg Val Gly Gly Lys Ser Lys His Gln Trp Arg
                    165                 170                 175

His Arg Asp Tyr Cys Ala Glu Ser Ile Ile Lys Thr Ala His Pro Leu
            180                 185                 190

Cys Thr Gly Lys Lys Thr Cys Lys Ile Ala His Asp Val Phe Leu Lys
            195                 200                 205

Asn Ala Lys Glu Cys Ile Pro Arg Glu Phe Asn Val Glu Tyr Tyr Cys
            210                 215                 220

Ala Ala Pro His Lys Asn Ser Phe Tyr Asp Pro Leu Asp Ala Val Val
225                 230                 235                 240

Val Asp Gly Val Ser Val Ala Thr Lys Tyr Val Leu Thr Ala Glu Asp
                    245                 250                 255

Gly Ala Arg Ala Ser Ala Lys Thr Asn Ala Tyr Gln Val Leu Gln Val
            260                 265                 270

Asp Ser Ala Leu Trp Glu Ser Asp Gly Ala Thr Glu Arg Arg Asp Arg
            275                 280                 285

Leu Glu Leu Val Lys Phe Leu Cys Asp Gly Arg Ala Glu Cys Val Phe
            290                 295                 300

Ser Pro Thr Arg Ser Ile Ile Gly Pro Asp Glu Arg Lys Cys Asn Asp
305                 310                 315                 320

Val Val Phe Gly Gly Met Val Lys Asp Thr Met Ser His Phe Met Leu
                    325                 330                 335

Arg Ala His Phe Ser Leu Val Pro Phe Asp Pro Lys Lys Tyr Asp Glu
            340                 345                 350

Lys Glu Tyr His His Val Thr Ile Lys Ser Thr Glu Lys Lys Thr Leu
            355                 360                 365

Glu Cys Pro Val Asn Met Ser Leu Thr Phe Tyr Val Ala Leu Trp Gly
            370                 375                 380

Gly Lys Ile Thr Asp Thr Ser Pro Leu Lys Gly Pro Lys His Phe Val
385                 390                 395                 400

Glu Val Asp Ile Asn Gly Glu Lys His Arg Tyr Ser Glu Ile Ile Asn
                    405                 410                 415

Ile Val Gly Thr Gln Cys Phe Gly Lys Ser Lys Cys Glu Ile Glu Pro
            420                 425                 430

Leu Lys Leu Lys Pro Pro Arg His Glu Lys Asp Leu Lys Glu Phe Pro

-continued

```
            435                 440                 445

Thr His Glu Gly Val Lys Lys Asp Asp His Gln Leu Glu Leu Tyr Tyr
    450                 455                 460

Lys Cys Ile Asp Leu Gln Thr Leu Pro Ser Leu Val Glu Ser Leu Ile
465                 470                 475                 480

Ser Asp Gly Pro Arg Tyr Pro Arg Glu Phe Ile Thr Pro Ile Gln Leu
                485                 490                 495

Ser Pro Asp Met Arg Ile Val Val Met Leu Asp Ile Tyr Gly Pro Thr
                500                 505                 510

Val Leu Glu Val Ala Asn Ala Leu Lys Leu Glu Ile Pro Val Ala Arg
                515                 520                 525

Thr Asn Glu Ile Lys Ile Ser Trp Lys Asp Ala Lys Ile Ser Gln Gly
    530                 535                 540

Ile Arg Leu Val Lys Asp Thr Arg Asn Tyr Val Phe Glu Phe Val Ile
545                 550                 555                 560

Gly Ala Glu Asp Tyr Ile His Met Thr Val Asn Ser Phe Asp Asn Asp
                565                 570                 575

Gly Ser Pro Met Ser Ile Pro Val Glu Phe Glu Ala Ser Lys Arg Ile
                580                 585                 590

Leu Asp Phe Ser Arg Gly Ile Glu Asp Phe Val Val Ala Thr Gly Glu
                595                 600                 605

Ile Thr Asn Phe Arg Ala Phe Ile Lys Ser
    610                 615

<210> SEQ ID NO 17
<211> LENGTH: 644
<212> TYPE: PRT
<213> ORGANISM: Babesia duncani BdHSP-70-1

<400> SEQUENCE: 17

Met Ala Ala Thr Ala Ile Gly Ile Asp Leu Gly Thr Thr Tyr Ser Cys
1               5                   10                  15

Val Ala Val Tyr Lys Asp Asn Asn Val Glu Ile Ile Pro Asn Asp Gln
                20                  25                  30

Gly Asn Arg Thr Thr Pro Ser Tyr Val Ala Phe Thr Asp Thr Glu Arg
            35                  40                  45

Leu Val Gly Asp Ala Ala Lys Asn Gln Glu Ala Arg Asn Pro Glu Asn
    50                  55                  60

Thr Val Phe Asp Val Lys Arg Leu Ile Gly Arg Arg Phe Asp Asp Pro
65                  70                  75                  80

Thr Val Gln Ser Asp Met Lys His Trp Pro Phe Lys Val Asn Ala Gly
                85                  90                  95

Ala Gly Cys Lys Pro Thr Ile Glu Val Thr Phe Glu Gly Gln Lys Lys
                100                 105                 110

Thr Phe His Pro Glu Glu Ile Ser Ser Met Val Leu Ile Lys Met Lys
            115                 120                 125

Glu Ile Ala Glu Ala Tyr Leu Gly Arg Pro Val Thr Asp Ala Val Ile
    130                 135                 140

Thr Val Pro Ala Tyr Phe Asn Asp Ser Gln Arg Gln Ala Thr Lys Asp
145                 150                 155                 160

Ala Gly Thr Ile Ala Gly Leu Asn Val Met Arg Ile Ile Asn Glu Pro
                165                 170                 175

Thr Ala Ala Ala Ile Ala Tyr Gly Leu Asp Lys Lys Gly Ser Thr Glu
                180                 185                 190
```

```
Lys Asn Ile Leu Ile Phe Asp Leu Gly Gly Gly Thr Phe Asp Val Ser
        195                 200                 205

Ile Leu Thr Ile Glu Asp Gly Ile Phe Glu Val Lys Ala Thr Thr Gly
        210                 215                 220

Asp Thr His Leu Gly Gly Glu Asp Phe Asp Asn Val Leu Val Glu His
225                 230                 235                 240

Cys Val Arg Asp Phe Met Arg Met Asn Gly Gly Lys Asn Leu Ala Thr
                245                 250                 255

Asn Lys Arg Ala Leu Arg Arg Leu Arg Thr His Cys Glu Arg Ala Lys
                260                 265                 270

Arg Val Leu Ser Ser Ser Thr Gln Ala Thr Ile Glu Leu Asp Ser Leu
                275                 280                 285

Phe Glu Gly Ile Asp Tyr Asn Thr Thr Ile Ser Arg Ala Arg Phe Glu
        290                 295                 300

Glu Met Cys Asn Glu Lys Phe Arg Ser Thr Leu Ile Pro Val Glu Lys
305                 310                 315                 320

Ala Leu Arg Asp Ala Asp Met Asp Lys Arg Lys Ile Asn Glu Val Val
                325                 330                 335

Leu Val Gly Gly Ser Thr Arg Ile Pro Lys Ile Gln Gln Leu Ile Lys
                340                 345                 350

Asp Phe Phe Asn Gly Lys Glu Pro Ser Arg Ser Ile Asn Pro Asp Glu
                355                 360                 365

Ala Val Ala Tyr Gly Ala Ala Val Gln Ala Ala Val Leu Ser Gly Asn
        370                 375                 380

Gln Ser Glu Lys Ile Gln Glu Leu Leu Leu Leu Asp Val Ala Pro Leu
385                 390                 395                 400

Ser Leu Gly Leu Glu Thr Ala Gly Gly Val Met Thr Val Leu Ile Lys
                405                 410                 415

Arg Asn Thr Thr Ile Pro Thr Lys Lys Thr Gln Ile Phe Thr Thr Asn
                420                 425                 430

Glu Asp Arg Gln Glu Gly Val Leu Ile Gln Val Phe Glu Gly Glu Arg
                435                 440                 445

Ala Met Thr Lys Asp Asn Asn Leu Leu Gly Lys Phe His Leu Ser Gly
        450                 455                 460

Ile Ala Pro Ala Pro Arg Gly Val Pro Gln Ile Glu Val Thr Phe Asp
465                 470                 475                 480

Ile Asp Ala Asn Gly Ile Leu Asn Val Thr Ala Met Asp Lys Ser Thr
                485                 490                 495

Gly Lys Ser Glu Gln Val Thr Ile Thr Asn Asp Lys Gly Arg Leu Ser
                500                 505                 510

Gln Thr Asp Ile Asp Arg Met Val Ala Glu Ala Glu Lys Phe Lys Glu
                515                 520                 525

Glu Asp Glu Arg Arg Lys Cys Cys Ile Glu Ser Lys His Lys Leu Glu
        530                 535                 540

Asn Tyr Leu Tyr Ser Met Arg Ser Thr Leu Asn Glu Asp Ala Val Lys
545                 550                 555                 560

Gln Lys Leu Ser Thr Glu Glu Leu Gln Asn Gly Leu Asn Thr Val Glu
                565                 570                 575

Glu Ala Ile Lys Trp Val Glu Asn Asn Gln Leu Ala Asn Gln Asp Glu
                580                 585                 590

Phe Glu Asp Lys Leu Lys Glu Val Glu Lys Ala Cys Ala Pro Leu Thr
        595                 600                 605

Ala Lys Met Tyr Gln Ala Ala Gly Gly Ala Gly Ala Gly Gly Met Pro
```

-continued

```
                610                 615                 620

Gly Asn Phe Gly Gly Ala Ala Ala Pro Pro Ser Gly Gly Pro Thr Val
625                 630                 635                 640

Glu Glu Val Asp

<210> SEQ ID NO 18
<211> LENGTH: 654
<212> TYPE: PRT
<213> ORGANISM: Babesia duncani BdHSP-70-2

<400> SEQUENCE: 18

Met Gln Met Phe Asn Arg Phe Leu Lys Ala Ser Val Ala Leu Leu Ala
1               5                   10                  15

Val Ala Ser Phe Gly Ile Gln Tyr Ile Phe Ala Lys Gly Ser Asn Ser
                20                  25                  30

Gly Lys Ile Glu Gly Pro Ile Ile Gly Ile Asp Leu Gly Thr Thr Tyr
            35                  40                  45

Ser Cys Val Gly Ile Tyr Lys Asn Gly Arg Val Glu Ile Ile Ala Asn
        50                  55                  60

Glu Met Gly Asn Arg Ile Thr Pro Ser Tyr Val Ser Phe Val Glu Gly
65                  70                  75                  80

Thr Gln Lys Val Gly Glu Ala Ala Lys Ser Glu Ala Thr Ile Asn Thr
                85                  90                  95

Glu Ser Thr Val Phe Asp Val Lys Arg Leu Ile Gly Arg Lys Phe Thr
                100                 105                 110

Asp Arg Asp Val Gln Glu Asp Met Lys Leu Leu Pro Tyr Lys Ile Ile
            115                 120                 125

Asn Lys Ser Thr Arg Pro Tyr Ile Ser Leu His Asp Gly Lys Glu Gln
        130                 135                 140

Arg Thr Phe Ala Pro Glu Glu Ile Ser Ala Met Val Leu Lys Lys Met
145                 150                 155                 160

Lys Gln Val Ala Glu Ser Tyr Leu Gly Lys Glu Val Lys Lys Ala Ile
                165                 170                 175

Ile Thr Val Pro Ala Tyr Phe Asn Asp Ser Gln Arg Gln Ser Thr Lys
                180                 185                 190

Asp Ala Gly Ala Ile Ala Gly Leu Asp Val Val Arg Ile Ile Asn Glu
            195                 200                 205

Pro Thr Ala Ala Ala Ile Ala Tyr Gly Leu Asp Lys Ala Asn Ala Glu
        210                 215                 220

Ser Asn Ile Leu Val Tyr Asp Leu Gly Gly Gly Thr Phe Asp Val Ser
225                 230                 235                 240

Val Leu Thr Leu Asp Ser Gly Val Phe Glu Val Ile Ala Thr Gly Gly
                245                 250                 255

Asp Thr His Leu Gly Gly Glu Asp Phe Asp Arg Arg Val Met Asp His
            260                 265                 270

Phe Ile Asp Ile Phe Lys Lys Lys His Lys Val Asn Ile Arg Asp Asn
        275                 280                 285

Lys Gln Ser Leu Gln Lys Leu Arg Lys Glu Val Glu Ala Ala Lys Arg
        290                 295                 300

Thr Leu Ser Ser Thr Thr Glu Val Leu Val Glu Val Glu Asn Leu Ile
305                 310                 315                 320

Asn Gly Ile Asp Phe Ser Glu Lys Leu Thr Arg Ala Lys Phe Glu Ser
                325                 330                 335

Leu Asn Ala Glu Leu Phe Glu Lys Thr Leu Ala Thr Val Lys Lys Val
```

```
                340                 345                 350

Val Glu Asp Ala Asp Ile Pro Ile Arg Asp Ile Asn Gln Val Val Leu
            355                 360                 365

Val Gly Gly Ser Thr Arg Ile Pro Arg Ile Arg Glu Met Ile Lys Glu
            370                 375                 380

Tyr Phe Gly Lys Glu Pro Asp Tyr Gly Ile Asn Pro Asp Glu Ala Val
385                 390                 395                 400

Ala Phe Gly Ala Ala Met Gln Gly Gly Ile Leu Ser Gly Glu Ser Ser
                405                 410                 415

Asp Asn Leu Leu Leu Leu Asp Val Cys Pro Leu Ser Leu Gly Ile Glu
            420                 425                 430

Thr Leu Gly Glu Val Met Ser Val Ile Ile Pro Arg Asn Thr Met Ile
            435                 440                 445

Pro Ala His Lys Ser Gln Val Phe Ser Thr Ser Val Asp Asn Gln Pro
            450                 455                 460

Met Val Thr Ile Lys Val Tyr Gln Gly Glu Arg Lys Leu Thr Lys Asp
465                 470                 475                 480

Asn Val Ile Leu Gly Lys Phe Asp Leu Ser Gly Ile Pro Pro Ala Pro
                485                 490                 495

Arg Gly Val Pro Gln Ile Glu Val Thr Phe Asp Ile Asp Thr Asn Gly
            500                 505                 510

Ile Leu Ser Val Ser Ala Glu Glu Lys Gly Ser Gly Asn Lys His Asn
            515                 520                 525

Ile Val Ile Thr Pro Asp Lys Gly Arg Leu Ser Pro Glu Glu Ile Glu
            530                 535                 540

Arg Met Ile Lys Asp Ala Glu Met Asn Ala Glu Lys Asp Lys Glu Val
545                 550                 555                 560

Phe Asn Arg Val Gln Ala Arg Gln Ala Leu Glu Gly Tyr Ile Asp Ser
                565                 570                 575

Met Thr Lys Thr Ile Asn Asp Asp Lys Thr Gly Lys Lys Leu Glu Asp
                580                 585                 590

Asp Glu Lys Glu Lys Ile Arg Asp Ala Leu Asp Glu Gly Thr Lys Trp
            595                 600                 605

Leu Ala Ser Asn Pro Glu Val Gly Ala Asp Glu Ile Ser Ala Lys Gln
            610                 615                 620

His Glu Ile Glu Ala Ile Cys Asn Pro Ile Ile Ser Lys Leu Tyr Gly
625                 630                 635                 640

Ser Gly Glu Asp Ser Asp Asp Ser Gly Tyr Ser Asp Glu Leu
                645                 650
```

<210> SEQ ID NO 19
<211> LENGTH: 612
<212> TYPE: PRT
<213> ORGANISM: Babesia duncani BdHSP-70-3

<400> SEQUENCE: 19

```
Met Ala Asp Arg Phe Thr Gly Arg Asn Asn Arg Glu Ala Val Val Ala
1                   5                   10                  15

Tyr Pro Gly Trp Phe Ser Glu Thr Gln Lys Gln Cys Leu Arg Ala Cys
                20                  25                  30

Val Thr Ala Ser Gly Leu Ser Cys Leu Arg Val Ile Ser His Val His
            35                  40                  45

Ala Met Ala Met Asp Tyr Gly Val Tyr Arg Val Lys Gln Leu Asn Asp
            50                  55                  60
```

-continued

```
Glu Thr Pro Thr Arg Val Ala Leu Val Met Ile Gly His Cys His Ala
65                  70                  75                  80

Ser Ala Ala Ile Val Asp Phe Tyr Ala Ser His Cys Ser Ile Leu Ser
                85                  90                  95

Gln Val Ser Arg Arg Asn Leu Gly Gly Arg Asn Leu Asp Met Met Leu
            100                 105                 110

Met Lys Tyr Met Ala Thr Glu Phe Ser Lys Lys Tyr His Cys Asp Pro
        115                 120                 125

Leu Glu Asn Asn Lys Thr Arg Leu Lys Val Glu Ala Val Ala Val Lys
        130                 135                 140

Thr Arg Arg Val Leu Ser Ala Asn Ala Glu Ser Ser Tyr Ser Ala Glu
145                 150                 155                 160

Cys Leu Met Glu Asp Asn Asp Met Ser Gly His Ile Thr Arg Thr Gln
                165                 170                 175

Phe Glu Glu Met Cys Asn Ala Glu Phe Ile Pro Gln Leu Ile Glu Met
                180                 185                 190

Leu Lys Glu Cys Ile Glu Ala Ser Arg Thr Asp Leu Asp Ser Ile Phe
            195                 200                 205

Ser Val Glu Ile Ala Gly Gly Ser Ser Arg Ile Pro Cys Ile Gln Gln
        210                 215                 220

Ala Ile Ser Ser Ile Phe Asn Lys Val Pro Ser Arg Thr Leu Asn Ala
225                 230                 235                 240

Asp Glu Cys Ile Ala Arg Gly Cys Val Leu Glu Ala Ala Ile Lys Ser
                245                 250                 255

Asn His Tyr Arg Val Arg Glu Tyr Lys Thr Arg Leu Thr Leu Pro Arg
            260                 265                 270

Ser Leu Thr Leu Gly Tyr Phe Asn Gly Gln Glu Pro Met Leu Leu Glu
        275                 280                 285

Ala Ile Ala Ala Gly Thr Pro Leu Gly Asp Pro Ile Arg Val Thr Leu
        290                 295                 300

Gln Ala Gln Ala Pro Val Cys Val Arg Val Ala Leu Gly Asp Ala Leu
305                 310                 315                 320

Asp Pro Arg Ser Gln Asp Ala Leu Gly Thr Leu Asp Ile Ala Arg His
            325                 330                 335

Ile Ser Gln Glu Ala Gln Pro Ala Pro Val Thr Thr Asn Asp Gly Ala
            340                 345                 350

Ala Ile Gln Thr Asp Glu Gln Asp Ala Glu Ile Gln Ser Glu Ser Ser
            355                 360                 365

Pro Ser Gly Gly Ile Ser Val Thr Leu Gly Phe Asp Asp Cys Gly Gln
        370                 375                 380

Phe Val Ala Ser Pro Glu Cys Cys Glu Tyr Arg Trp Leu Pro Ala Thr
385                 390                 395                 400

Ile Leu Asp Ile Ala Arg Leu Glu Ala Ala Glu Leu Glu Ala Arg Gly
            405                 410                 415

Arg Asp Leu Lys Glu Asn Ser Arg Leu Gln Ala Leu Asn Asp Phe Glu
            420                 425                 430

Thr Leu Leu Tyr Thr Val Arg Asp Lys Met Gln Ser Ser His Arg Asp
        435                 440                 445

Phe Ile Asp Pro Gln Met Ile Pro Ala Tyr Glu Ser Glu Leu Asp His
        450                 455                 460

Trp Arg Glu Trp Leu Tyr Glu Asn Ser Gly Ala Ser Gln Glu Thr Leu
465                 470                 475                 480

Gln Glu Gly Ile Asp Lys Val Ser Ser Glu Trp Lys Arg Ile Asp Lys
```

-continued

```
              485                  490                  495

Tyr Phe Lys Glu His Gln Asn Lys Leu Glu Asn Leu Glu Pro Phe Leu
            500                  505                  510

Gln Arg Leu Gln Glu Arg Tyr Asn Phe Cys Cys Glu Asp Asn Asn Pro
            515                  520                  525

Asn Trp His Gly Ala Thr Pro Glu Glu Arg Leu Asn Phe Ala Gln Glu
        530                  535                  540

Leu Met Asp Leu Asp Ser Arg Val Arg Gln Met His Gln Asp Glu Ser
545                  550                  555                  560

Gln Arg Pro Arg His Met Glu Pro Leu Phe Thr Met Gln Gln Ile Gln
                565                  570                  575

Gly Glu Met Gln Lys Leu Leu Val Ser Ile Ser Glu Phe Cys Gln Ala
            580                  585                  590

Lys Ala Ala Lys Ala Pro Ala Gln Glu Pro Pro Glu Gln Gln Pro Lys
            595                  600                  605

Glu Gln Gln Glu
        610
```